(12) United States Patent
Williams

(10) Patent No.: US 11,744,808 B2
(45) Date of Patent: Sep. 5, 2023

(54) COMPOSITIONS AND METHODS FOR TREATING NON-ALCOHOLIC STEATOHEPATITIS

(71) Applicant: ALGERNON PHARMACEUTICALS INC., Vancouver (CA)

(72) Inventor: Mark Williams, Winnipeg (CA)

(73) Assignee: ALGERNON PHARMACEUTICALS INC., Vancouver (CA)

( * ) Notice: Subject to any disclaimer, the term of this patent is extended or adjusted under 35 U.S.C. 154(b) by 0 days.

(21) Appl. No.: 17/258,402

(22) PCT Filed: Jul. 3, 2019

(86) PCT No.: PCT/CA2019/050915
§ 371 (c)(1),
(2) Date: Jan. 6, 2021

(87) PCT Pub. No.: WO2020/006631
PCT Pub. Date: Jan. 9, 2020

(65) Prior Publication Data
US 2021/0290566 A1      Sep. 23, 2021

Related U.S. Application Data

(60) Provisional application No. 62/809,351, filed on Feb. 22, 2019, provisional application No. 62/694,848, filed on Jul. 6, 2018.

(51) Int. Cl.
*A61K 31/136*  (2006.01)
*A61K 31/167*  (2006.01)
*A61P 1/16*    (2006.01)

(52) U.S. Cl.
CPC .......... *A61K 31/136* (2013.01); *A61K 31/167* (2013.01); *A61P 1/16* (2018.01)

(58) Field of Classification Search
CPC .................................................. A61K 31/136
See application file for complete search history.

(56) References Cited

FOREIGN PATENT DOCUMENTS

WO    2012157290 A1    11/2012

OTHER PUBLICATIONS

Takei et al., "Mechanism of Action of MY-1250, an activate metabolite of Repirinast, in inhibiting histamine release from rat mast cells", Br. J. Pharmacol, pp. 587-590, Mar. 1992 (Year: 1992).*
"Fatty Liver Disease", Medline, pp. 1-6, Apr. 26, 2017 (Year: 2017).*
Kennedy et al., "Blocking Hw/H2 Histamine Receptors Inhibits Damage/Fibrosis in—Mdr2-/- mice and Human Cholangiocarcinoma Tumorigenesis", Hepatology, vol. 68, No. 3, Mar. 12, 2018 (Year: 2018).*
Horii et al., "Cardiovascular effects of MY-5116 and MY-1250", Nihon Yakurigaku Zasshi, Apr. 1986 (Year: 1986).*
M. Fang et al: "Effect of cepharanthine hydrochloride on lipid metabolism and peroxidation against acute fatty liver in mice"; Zhonghua Zhongyiyao Zazhi (2011), 26(6), 1429-1432.
International Search Report and Written Opinion, PCT/CA2019/050915, dated Sep. 9, 2019, 10 pages.
Bosch MD, PhD, D. et al., "Primary Sclerosing Cholangitis is Protective Against Non-alcoholic Fatty Liver Disease in Inflammatory Bowel Disease," Human Pathology, 22 pages (2017).
Dascal R. et al., "Unconjugated hyperbilirubinemia may exacerbate certain underlying chronic liver diseases," Canadian Liver Journal, vol. 4(5): 446-452 (2022).
Doycheva, I. et al., "Prevalence and Relevance of Nonalcoholic Fatty Liver Disease in Patients with Primary Sclerosing Cholangitis," Dig Dis Sci., vol. 59(7):1645-1646. doi: 10.1007/s10620-014-3051-4 (2014).
Lin, L. et al., "Diet-Induced Obesity Disrupts Histamine-Dependent Oleoylethanolamide Signaling in the Mouse Liver," Pharmacology, vol. 107:423-432 (2022).
Yamada, S. "Novel function of histamine signaling via histamine receptors in cholesterol and bile acid metabolism: Histamine H2 receptor protects against nonalcoholic fatty liver disease," Pathology International, vol. 66: 376-385 (2016).

* cited by examiner

*Primary Examiner* — John S Kenyon
*Assistant Examiner* — Gillian A Hutter
(74) *Attorney, Agent, or Firm* — Nelson Mullins Riley & Scarborough LLP; Anthony A. Laurentano

(57) ABSTRACT

Cepharanthine, Repirinast, Ifenoprodil Hemitartrate, Bromantane, Actarit, Lobenzarit, Irsogladine, Istradefylline, Trapadil, Bemithyl, and are used for treating or prophylaxis of lobular inflammation, non-alcoholic fatty liver disease or non-alcoholic steatohepatitis in a subject.

6 Claims, 22 Drawing Sheets

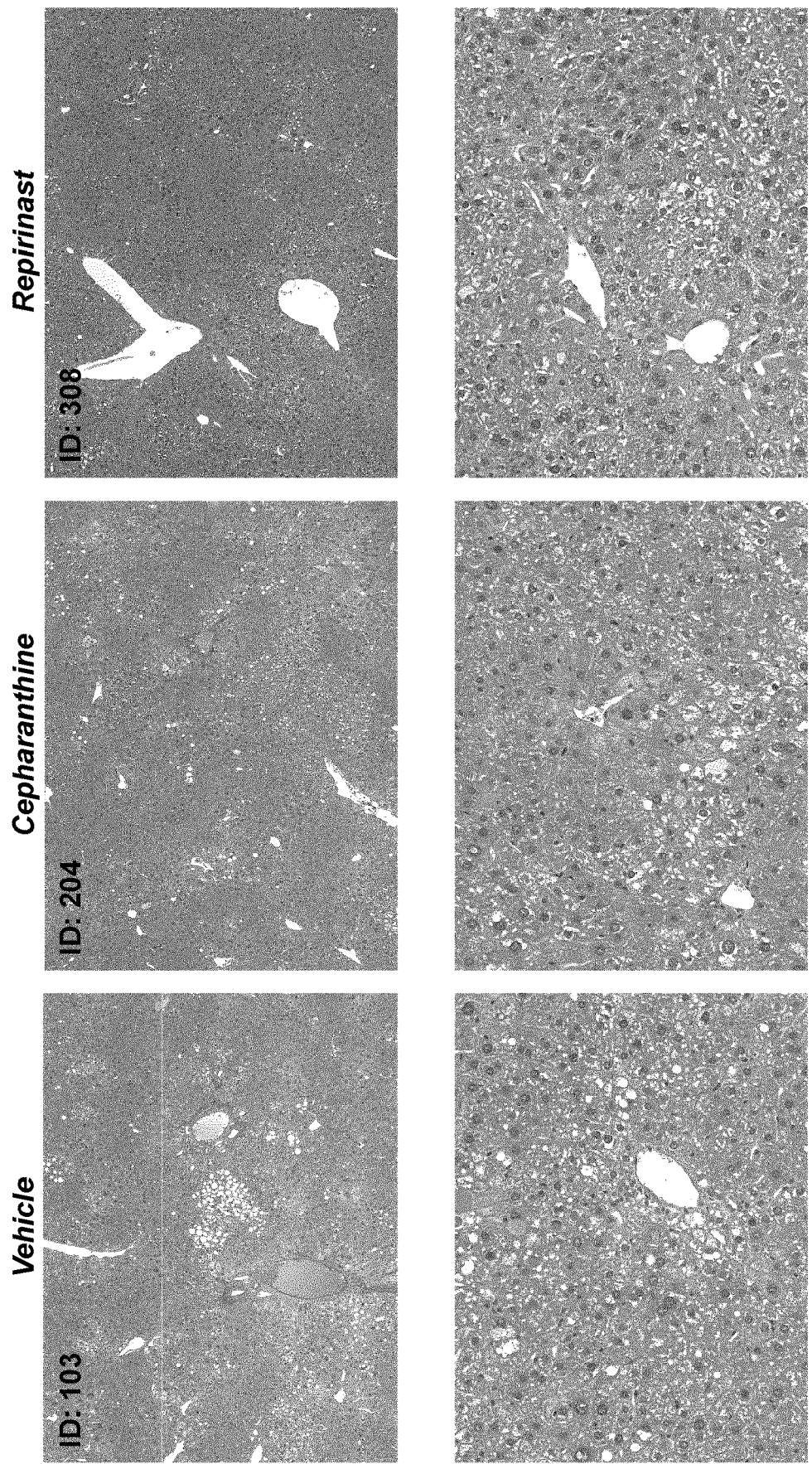

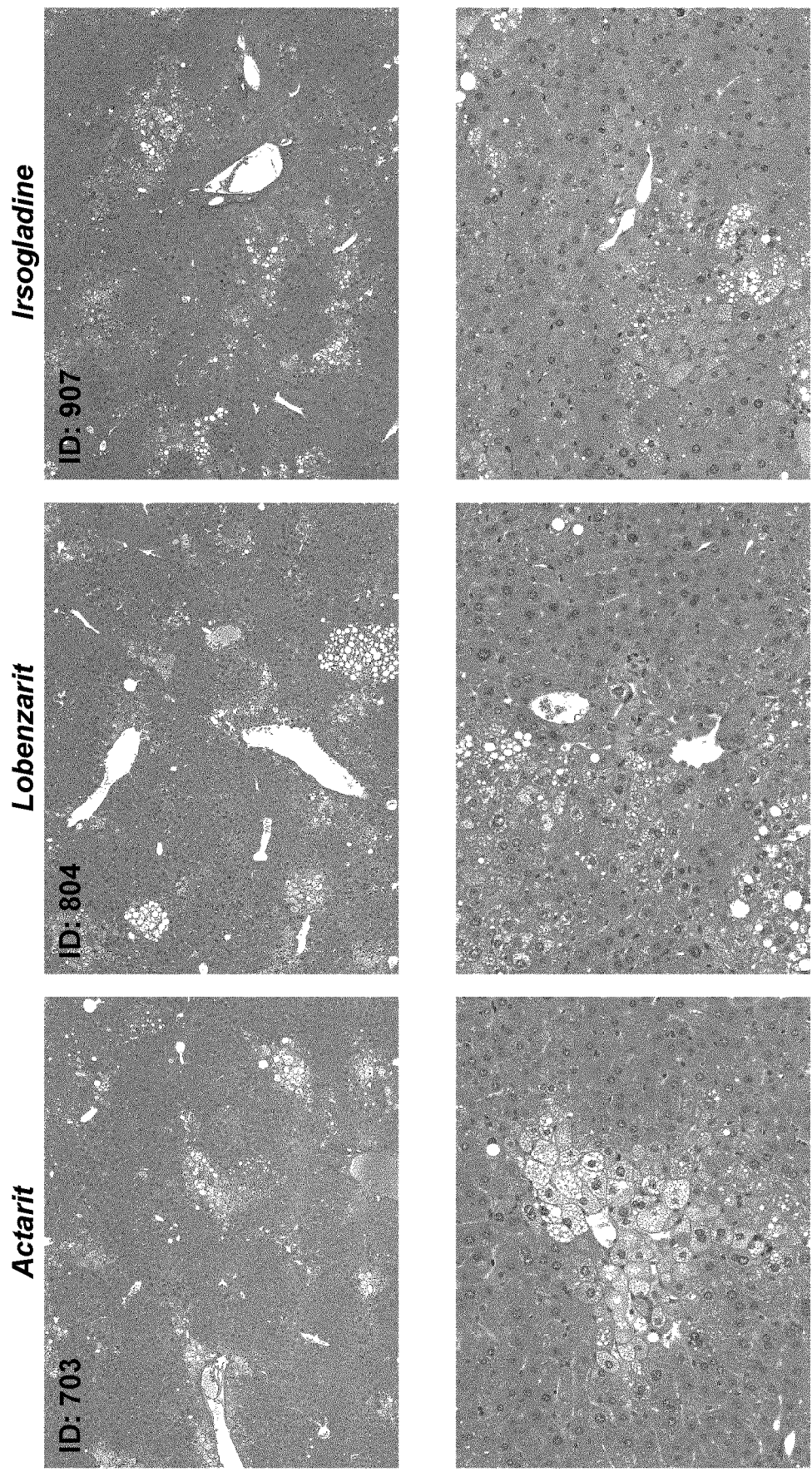

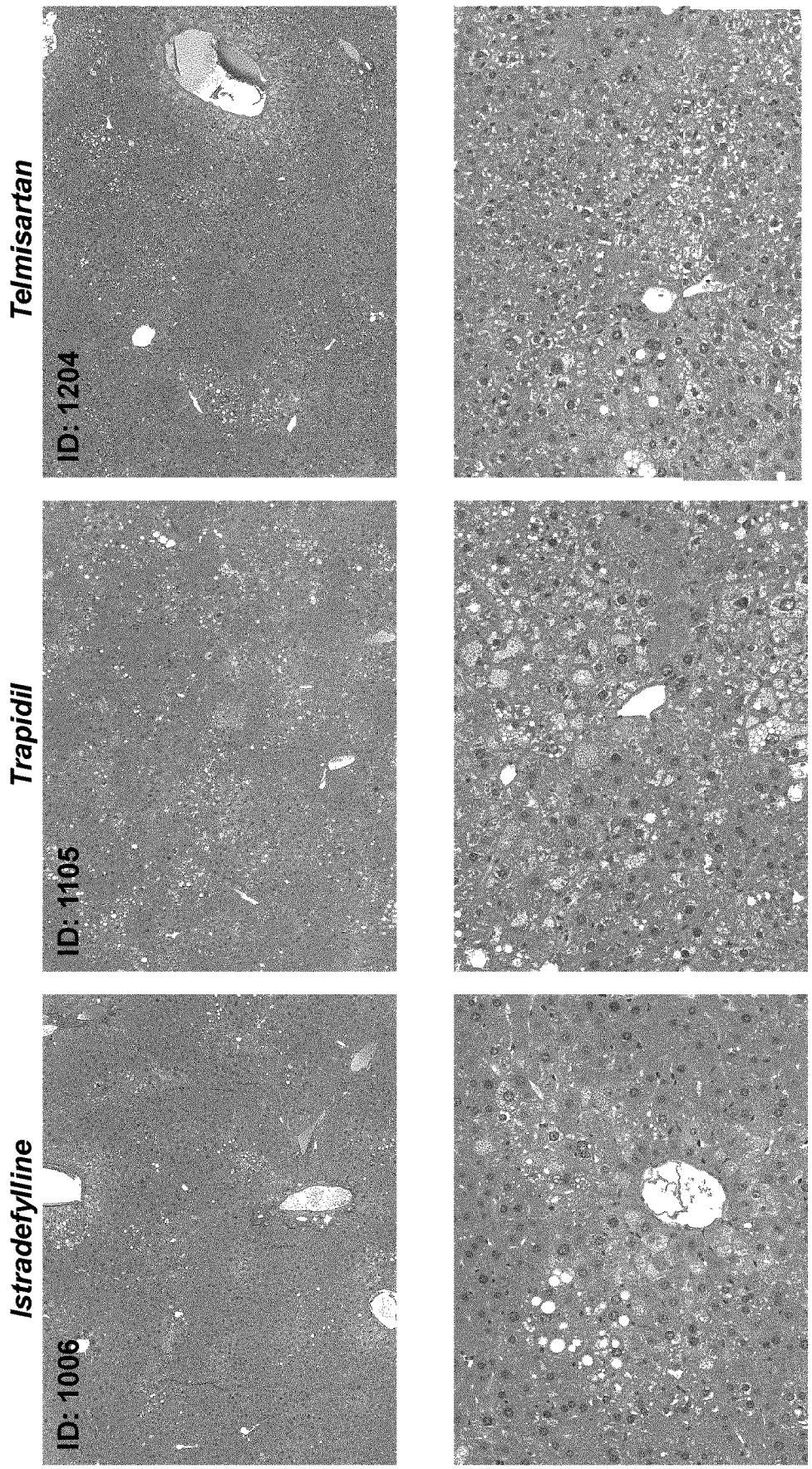

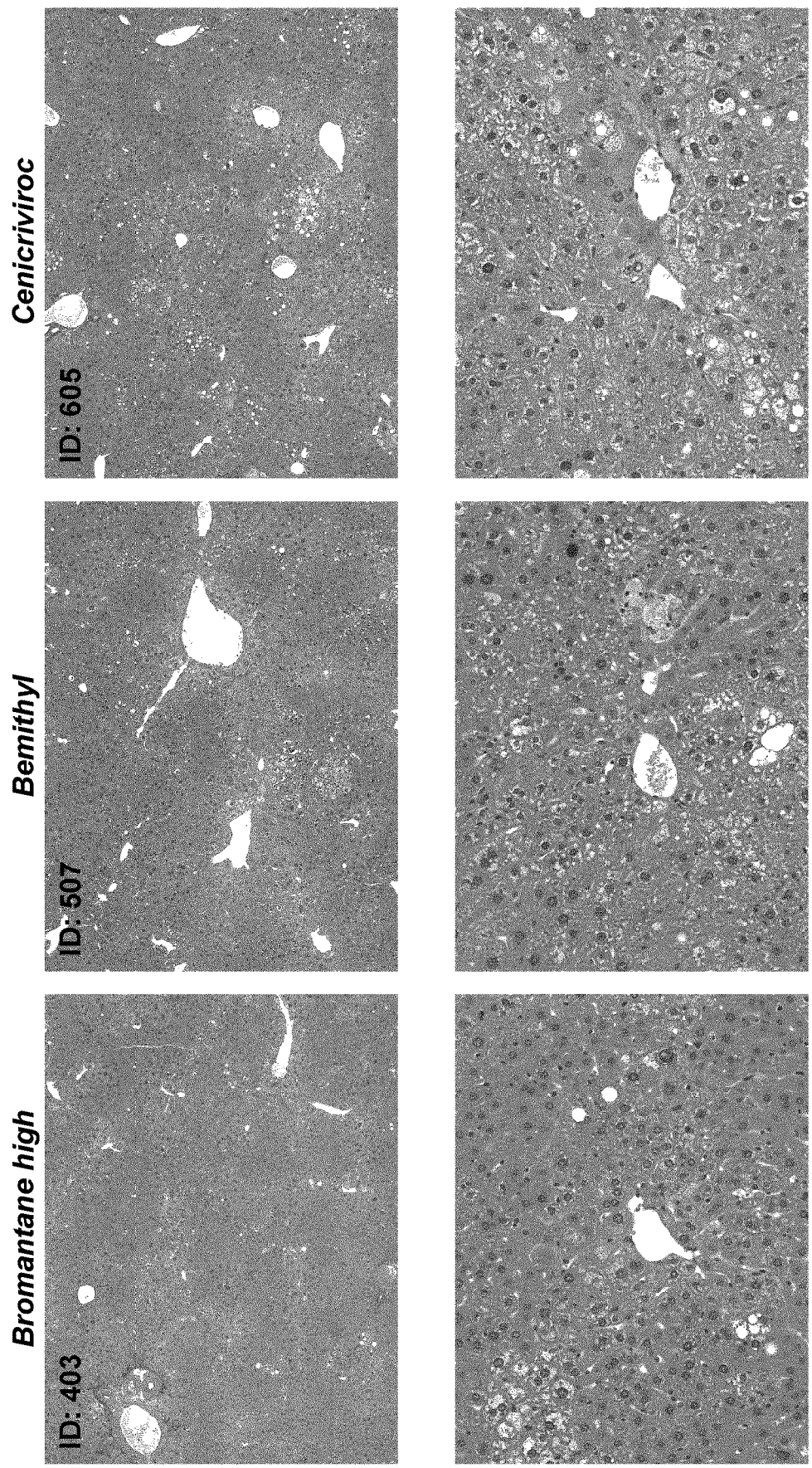

COMPOSITIONS AND METHODS FOR TREATING NON-ALCOHOLIC STEATOHEPATITIS

REFERENCE TO RELATED APPLICATIONS

This application is a 35 U.S.C. 371 national stage filing of International Application No. PCT/CA2019/050915, filed on Jul. 3, 2019, which claims priority from U.S. provisional application No. 62/694,848 filed Jul. 6, 2018 and U.S. provisional application No. 62/809,351 filed Feb. 22, 2019, the contents of which are hereby incorporated by reference.

FIELD OF INVENTION

The present invention relates to the use of compounds for treating non-alcoholic fatty liver disease, and in particular, the use of particular test compounds for treating non-alcoholic fatty liver disease, non-alcoholic fatty liver, and non-alcoholic steatohepatitis.

BACKGROUND

Non-alcoholic fatty liver disease (NAFLD) covers a range of liver conditions characterized by too much fat stored in liver cells. As its name implies, the causes are generally unrelated to alcohol consumption. This is in contrast to alcoholic liver disease, which is caused by heavy alcohol use. Most commonly, NAFLD is either non-alcoholic simple fatty liver or non-alcoholic steatohepatitis (NASH).

Nonalcoholic fatty liver is a condition where you have fat in your liver but little or no inflammation or liver cell damage. It typically does not progress to cause liver damage or complications.

NASH includes both a fatty liver and liver inflammation. While those with only nonalcoholic fatty liver are generally asymptomatic, the inflammation and liver cell damage with NASH can cause fibrosis, or scarring, of the liver, and in severe cases, may lead to cirrhosis (advanced scarring) or liver cancer. In that regard, common signs and symptoms of NASH and cirrhosis can include abdominal swelling, enlarged blood vessels just beneath the skin's surface, enlarged breasts in men and jaundice.

Factors which increase one's risk of NASH include diabetes, obesity, a high fructose diet, genetics and advanced age. While improving one's diet and exercise are an efficient way to manage NAFLD and reduce insulin resistance, there is currently no cure for NAFLD or NASH, and there is no single treatment that works for every individual. Drugs currently used to treat NAFLD and NASH may help to increase fat loss and/or improve biomedical marker levels, but none have been shown to reverse or reduce NAFLD and NASH once liver scarring has begun.

The murine models of NAFLD and NASH are well-characterized experimental models of metabolically-induced hepatic injury that ultimately lead to spontaneous hepatic steatosis—a common characteristic of many chronic hepatitis disorders. In the dietary models, the progression towards fatty liver is highly predictable and reproducible, leading to steatosis based on insulin resistance and obesity (Ishii et al, *Female spontaneously diabetic Torii fatty rats develop nonalcoholic steatohepatitis-like hepatic lesions,* World J Gastroenterol, 21(30):9067-78 (2015); Kucera 0 and Cervinkova Z, *Experimental models of non-alcoholic fatty liver disease in rats,* World J Gastroenterol, 20(26): 8364-76 (2014); Takahashi et al, *Animal models of nonalcoholic fatty liver disease/nonalcoholic steatohepatitis,* World J Gastroenterol, 18(19); 2300-08 (2012)).

In one such model (known as the Stelic Animal Model or STAM$^{TM}$) of NASH-derived hepatocellular carcinoma ("NASH-HCC") in mice, subcutaneous streptozotocin ("STZ") exposure followed by a continuous high-fat diet leads to diabetes, significant steatosis, chronic lobular inflammation, pericellular fibrosis, liver cirrhosis and HCC resembling the entire cascade of human NASH-HCC in a relatively short period of 6 to 16 weeks, including moderate increases of transaminases and plasma lipids—major hallmarks of human NASH (Fujii M et al, *A murine model for non-alcoholic steatohepatitis showing evidence of association between diabetes and hepatocellular carcinoma,* Med Mol Morphol, 46(3):141-52 (2013)).

The present invention provides a novel use of existing drugs, typically studied as potential therapies for other pathologies, for the treatment and/or alleviation of NAFLD and NASH.

SUMMARY OF INVENTION

In one embodiment, the present invention provides methods and uses of Cepharanthine in the prophylaxis or treatment of lobular inflammation or non-alcoholic fatty liver disease in a subject.

In another embodiment, the present invention provides methods and uses of Repirinast in the prophylaxis or treatment of lobular inflammation or non-alcoholic fatty liver disease in a subject.

In another embodiment, the present invention provides methods and uses of Ifenprodil Hemitartrate in the prophylaxis or treatment of lobular inflammation or non-alcoholic fatty liver disease in a subject.

In another embodiment, the present invention provides methods and uses of Bromantane in the prophylaxis or treatment of lobular inflammation or non-alcoholic fatty liver disease in a subject.

In another embodiment, the present invention provides methods and uses of Suplatast Tosylate in the prophylaxis or treatment of lobular inflammation or non-alcoholic fatty liver disease in a subject.

In another embodiment, the present invention provides methods and uses of Actarit in the prophylaxis or treatment of lobular inflammation or non-alcoholic fatty liver disease in a subject.

In another embodiment, the present invention provides methods and uses of Lobenzarit in the prophylaxis or treatment of lobular inflammation or non-alcoholic fatty liver disease in a subject.

In another embodiment, the present invention provides methods and uses of Irsogladine in the prophylaxis or treatment of lobular inflammation or non-alcoholic fatty liver disease in a subject.

In another embodiment, the present invention provides methods and uses of Istradefylline in the prophylaxis or treatment of lobular inflammation or non-alcoholic fatty liver disease in a subject.

In another embodiment, the present invention provides methods and uses of Trapadil in the prophylaxis or treatment of lobular inflammation or non-alcoholic fatty liver disease in a subject.

In another embodiment, the present invention provides methods and uses of Bemithyl in the prophylaxis or treatment of lobular inflammation or non-alcoholic fatty liver disease in a subject.

In another embodiment, the present invention provides methods and uses of Cenicriviroc in the prophylaxis or treatment of lobular inflammation or non-alcoholic fatty liver disease in a subject.

In a further aspect, the non-alcoholic fatty liver disease is non-alcoholic steatohepatitis.

In an embodiment of the invention, the non-alcoholic fatty liver disease is non-alcoholic steatohepatitis-derived hepatocellular carcinoma.

BRIEF DESCRIPTION OF THE FIGURES

Exemplary embodiments are illustrated in referenced figures of the drawings. It is intended that the embodiments and figures disclosed herein are to be considered illustrative rather than restrictive.

FIGS. 2a, 2b, 2c, and 2d show representative photomicrographs of HE-stained liver sections for each of the 12 study groups of C57BL/6 mice consisting of the "Vehicle" control group and the 11 treatment groups including the positive control treatment group, Telmisartan. Upper panels are taken at ×50 magnification. Lower panels are ×200 magnification. The identity of each study group is listed above the upper panel in each pair of panels.

FIGS. 10a, 10b, and 10c show representative photomicrographs of HE-stained liver sections for each of the 7 study groups of C57BL/6 mice consisting of the Normal (no NASH) group, the "Vehicle" control group and the 5 treatment groups including the positive control treatment group, Telmisartan. Upper panels are taken at ×50 magnification. Lower panels are ×200 magnification. The identity of each study group is listed above the upper panel in each pair of panels.

DETAILED DESCRIPTION

Figure 1:
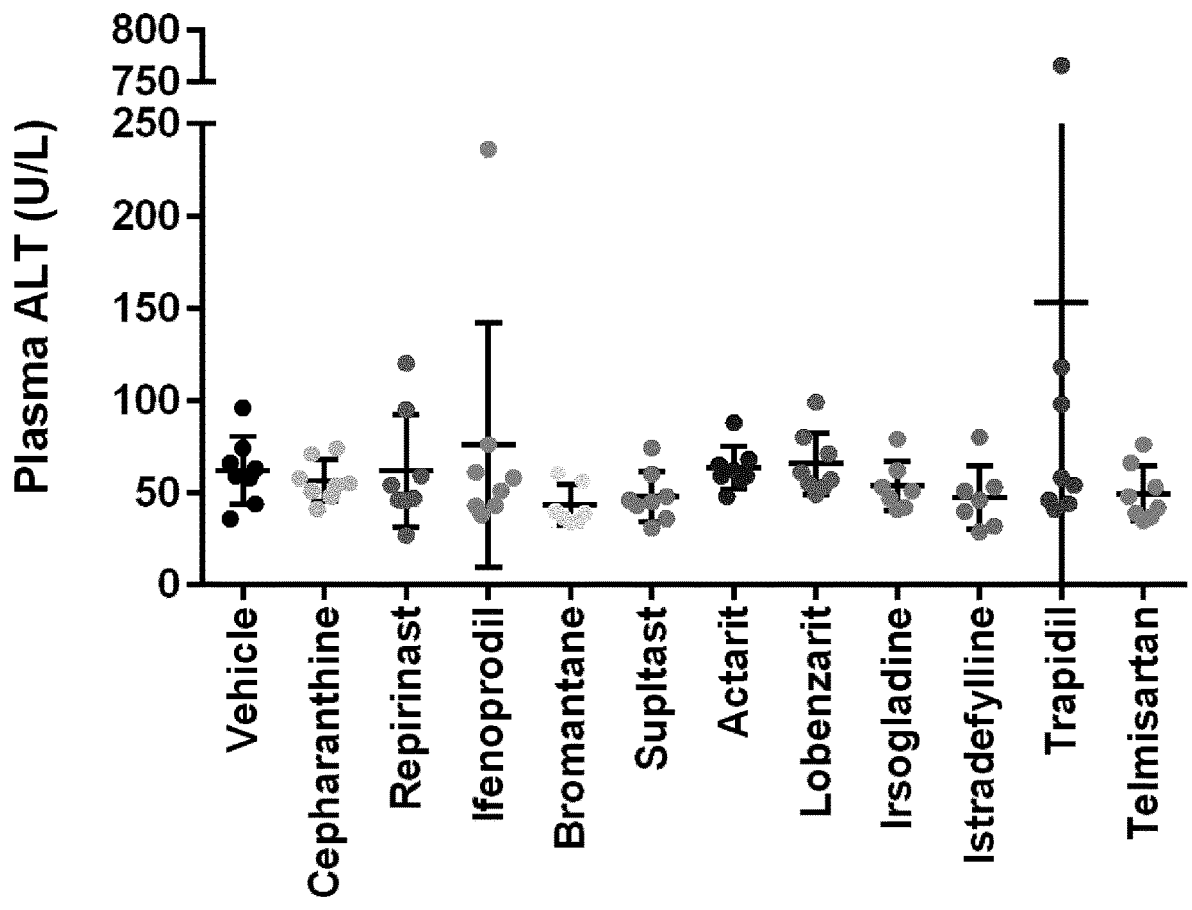
FIG. 1 shows an evaluation of liver function and disease progression consisting of the Plasma Alanine Aminotransferases (ALT) in units/L for each of 12 study groups in a first study of C57BL/6 mice consisting of the "Vehicle" control group and 11 treatment groups including the positive control treatment group, Telmisartan. Mean is indicated±SD as determined using the Bonferroni multiple comparison test.
Figure 2B:
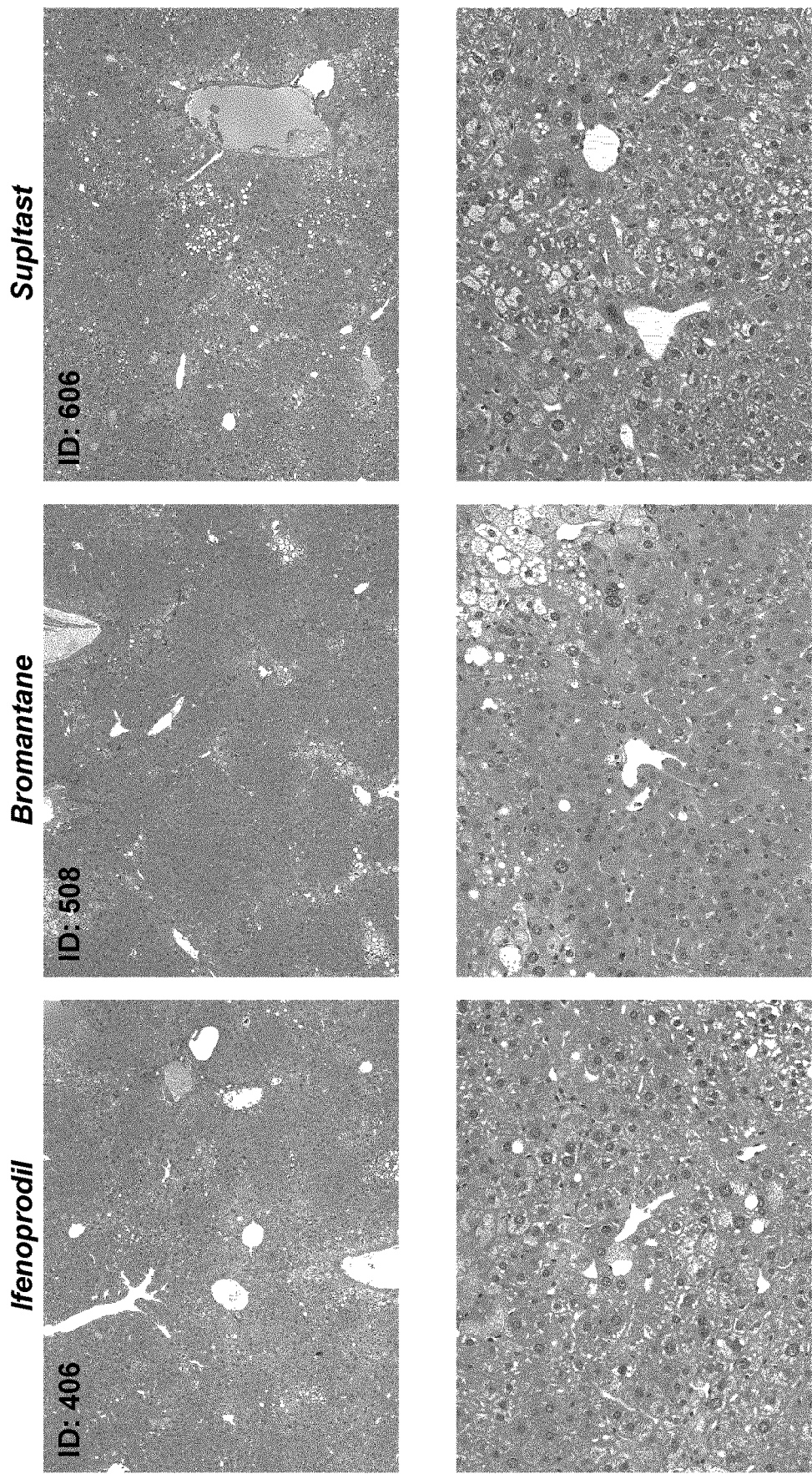
Figure 3:
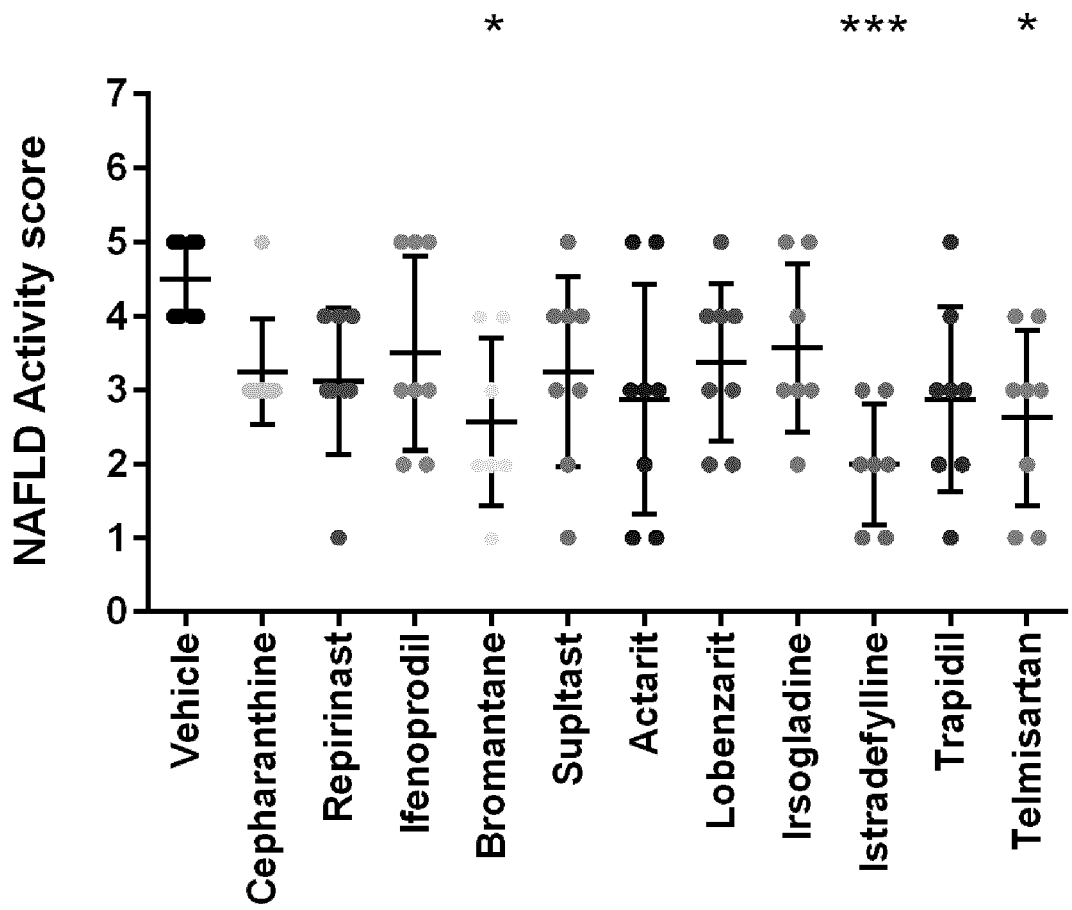
FIG. 3 shows the NAFLD activity score for each of the 12 study groups of C57BL/6 mice consisting of the "Vehicle" control group and the 11 treatment groups including the positive control treatment group, Telmisartan. Mean is indicated±SD as determined using the Bonferroni multiple comparison test.
Figure 4:
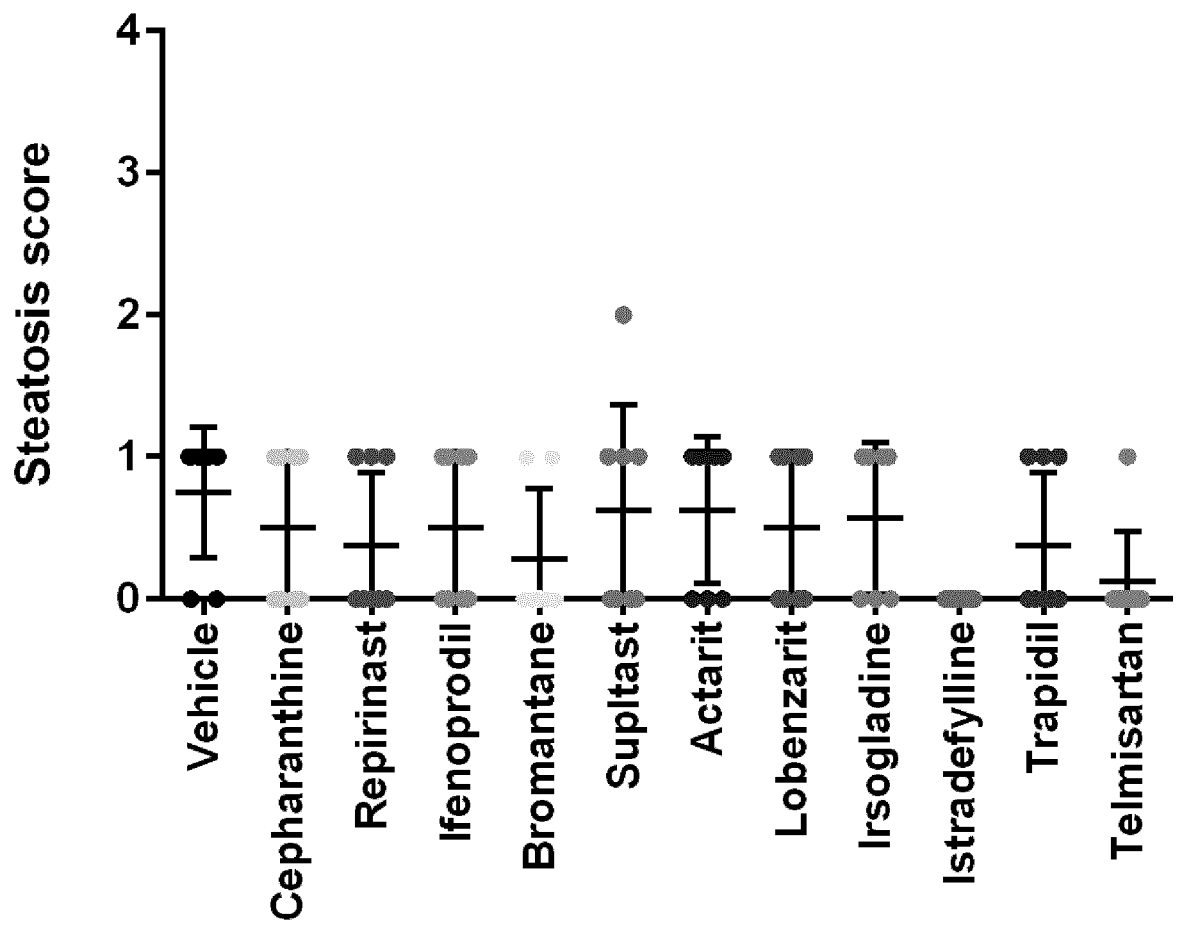
FIG. 4 shows the steatosis score for each of the 12 study groups of C57BL/6 mice consisting of the "Vehicle" control group and the 11 treatment groups including the positive control treatment group, Telmisartan. Mean is indicated±SD as determined using the Bonferroni multiple comparison test.
Figure 5:
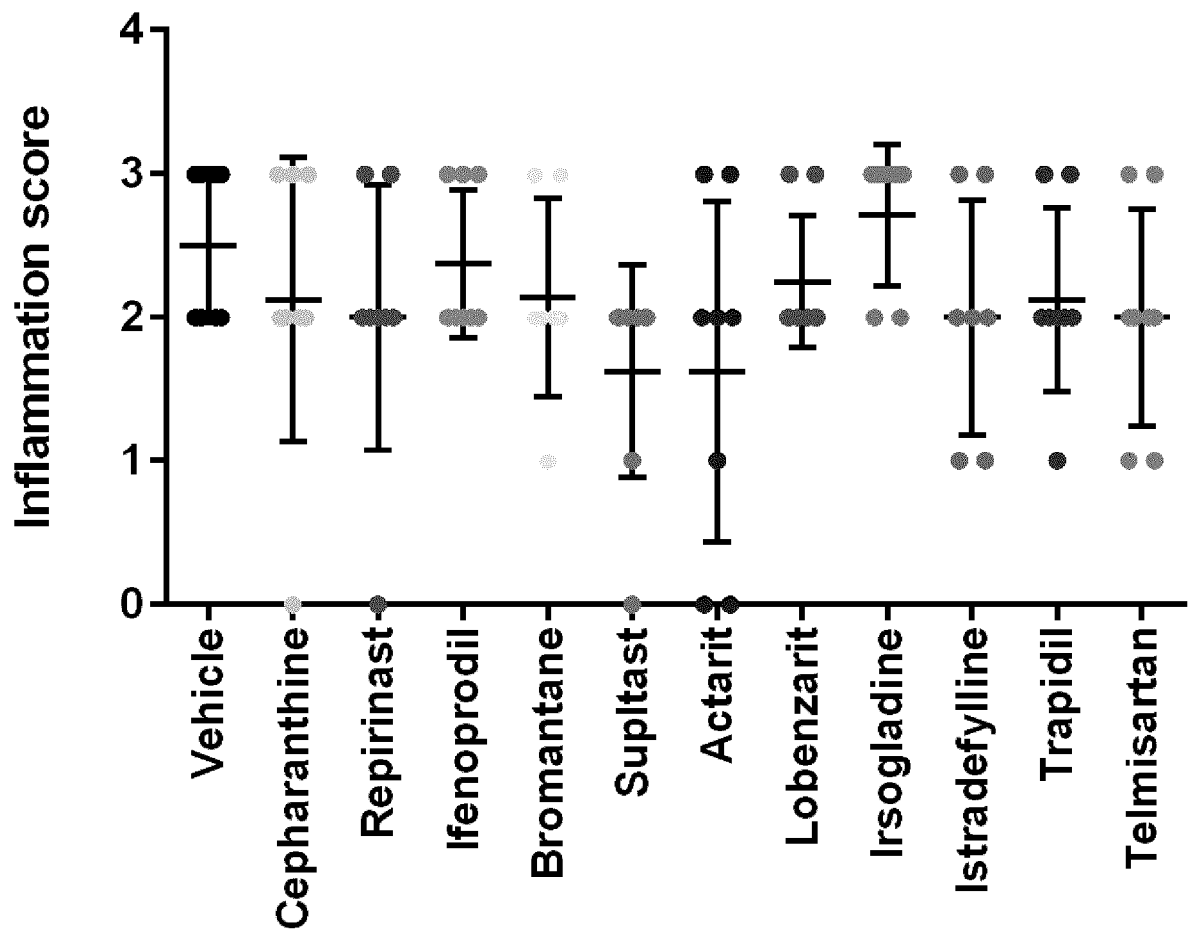
FIG. 5 shows the lobular inflammation score for each of the 12 study groups of C57BL/6 mice consisting of the "Vehicle" control group and the 11 treatment groups including the positive control treatment group, Telmisartan. Mean is indicated±SD as determined using the Bonferroni multiple comparison test.
Figure 6:
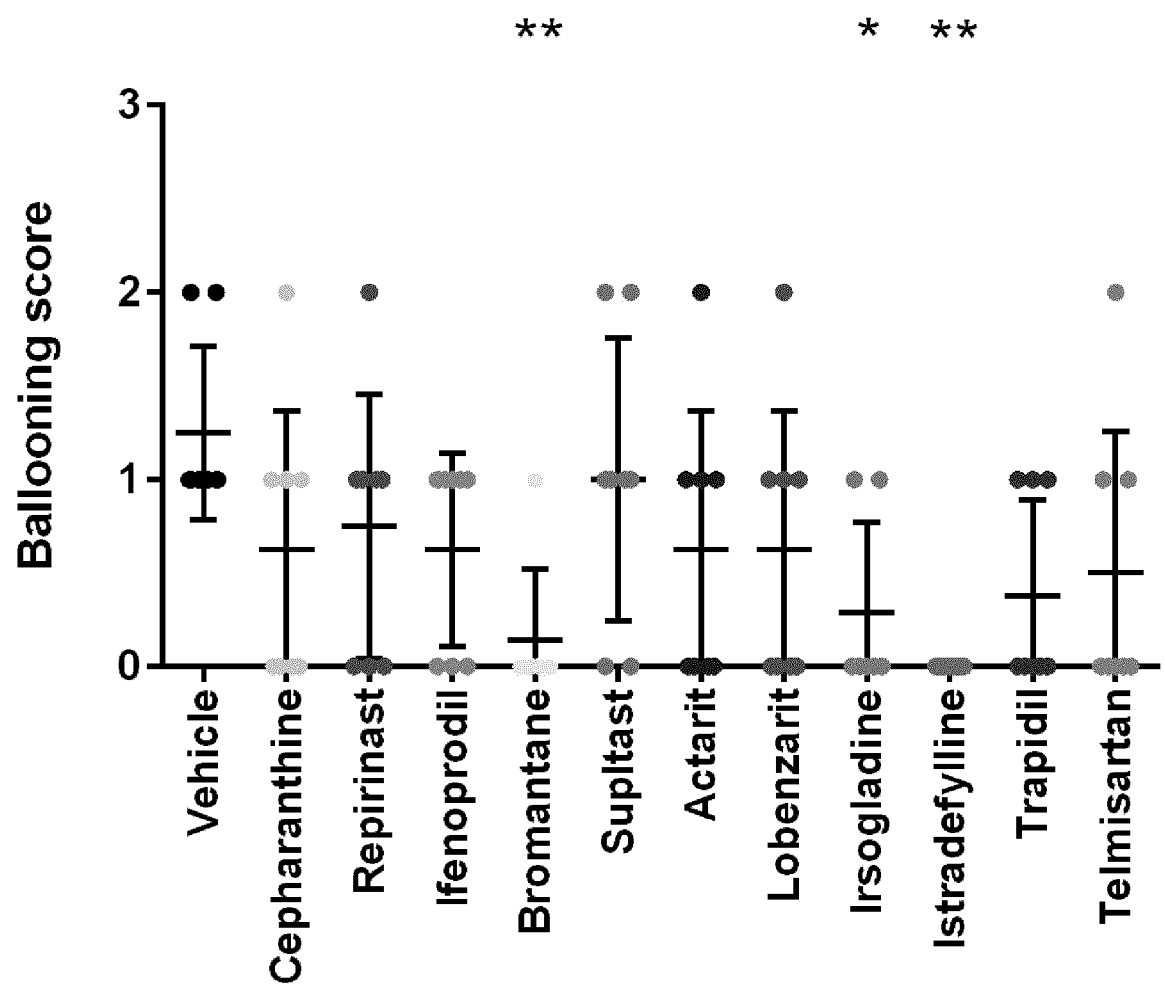
FIG. 6 shows the hepatocellular ballooning score for each of the 12 study groups of C57BL/6 mice consisting of the "Vehicle" control group and the 11 treatment groups including the positive control treatment group, Telmisartan. Mean is indicated±SD as determined using the Bonferroni multiple comparison test.

The inventor has found that a number of pharmacologic compounds approved for use in other pathologies are useful as an active ingredient in inhibiting or alleviating hepatic steatosis, lobular inflammation and hepatocellular ballooning and may be useful in the prophylaxis and/or treatment of NASH. In some embodiments, it is found that in the murine STAM™ model of NASH-HCC, the level of hepatic steatosis, lobular inflammation and hepatocellular ballooning is inhibited or alleviated. Based on the experimental results described herein, it is shown that the compounds described herein will be useful in some embodiments in the prophylaxis and/or treatment of NASH and/or NASH-derived HCC.

The examples and data below show the effects of inhibiting or alleviating hepatic steatosis, lobular inflammation and hepatocellular ballooning in two studies. In the first study, a therapeutically effective amount of 10 pharmacologic compounds was administered. In the second study, a therapeutically effective amount of 5 pharmacologic compounds were administered. The pharmacologic compounds, hereinafter known as "test agents", are approved for use in other pathologies, and are formulated with a pharmaceutically acceptable vehicle for the purpose of delivery and absorption.

A currently proposed therapy for treating NAFLD and NASH is administering the pharmacologic compound Telmisartan (Gitto et al, *Treatment of nonalcoholic steatohepatitis in adults: present and future, Gastroenterol Res Pract,* 2015:732870 (2015); Paschos P and Tziomalos K, *Nonalcoholic fatty liver disease and the renin-anaiotensin system: Implications for treatment, World J Hepatol.* 4(121:327-31 (2012); Musso G et al, *A meta-analysis of randomized trials for the treatment of nonalcoholic fatty liver disease, Hepatology,* 52(1):79-104 (2010); Georgescu E F et al, *Angiotensin-receptor blockers as therapy for mild-to-moderate hypertension-associated non-alcoholic steatohepatitis, World J Gastroenterol,* 15(8):942-54 (2009)), which was used as a positive control in the experimental examples described herein.

Telmisartan, 2-(4-{[4-Methyl-6-(1-methyl-1H-1,3-benzodiazol-2-yl)-2-propyl-1H-1,3-benzodiazol-1-yl] methyl}phenyl)benzoic acid, is an angiotensin receptor blocker known in the art for treating hypertension. The chemical structure of Telmisartan is:

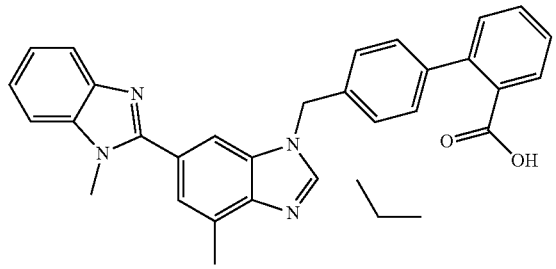

In animal models of NASH-HCC as described herein, a therapeutically effective amount can be typically calculated as the animal equivalent daily dose of the maximum daily human dose.

Use of Cepharanthine

Cepharanthine, (14S,27R)-22,33-Dimethoxy-13,28-dimethyl-2,5,7,20-tetraoxa-13,28-diazaoctacyclo[25.6.2. $2^{16,19}.1^{3,10}.1^{21,25}.0^{4,8}.0^{14,39}.0^{31,35}$]nonatriaconta-1(33),3,8,10(39),16,18,21(36),22,24,31,34,37-dodecaene, is an anti-inflammatory and anti-neoplastic compound known in the art for treating radiation-induced leukopenia, idiopathic thrombocytopenic purpura, alopecia areata and pityrodes, xerostomia, sarcoidosis, refractory anemia, and various cancer-related conditions. The chemical structure of Cepharanthine is:

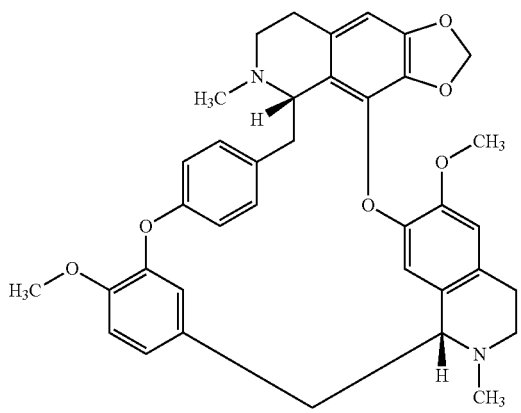 [SMILES: COc1ccc2cc1Oc1ccc(cc1)C[C@H]1c3c(cc4c(c3Oc3cc5c(cc3OC)CCN(C)[C@@H]5C2)OCO4)CCN1C]

In one aspect, the present invention provides a use and method of treatment or prophylaxis of lobular inflammation or non-alcoholic fatty liver disease in a subject with Cepharanthine or a pharmaceutically acceptable variation thereof. The non-alcoholic fatty liver disease may be NASH or NASH-HCC.

In an embodiment, the amount of Cepharanthine used is between 0.5 and 10 mg per kg of the subject. In a preferred embodiment, the amount of Cepharanthine used is between 1 to 4 mg per kg of the subject. In a further preferred embodiment, the amount of Cepharanthine used is about 2.25 mg per kg of the subject. In a further preferred embodiment, the amount of Cepharanthine used is about 2.5 mg per kg of the subject.

The Cepharanthine, or pharmaceutically acceptable variation thereof, may be administered to the subject orally, intravenously or in a manner known in the art. The Cepharanthine, or pharmaceutically acceptable variation thereof, may also be administered with one or more pharmaceutically acceptable excipients.

Use of Repirinast

Repirinast, 3-methylbutyl 7,8-dimethyl-4,5-dioxo-5,6-dihydro-4H-pyrano[3,2-c]quinoline-2-carboxylate, is known in the art as an antihistamine. The chemical structure of Repirinast is:

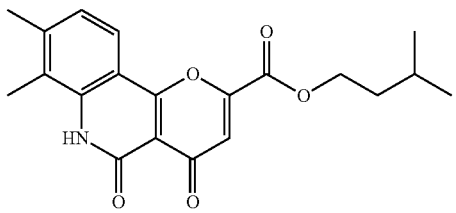 [SMILES: Cc1ccc2c([nH]c(=O)c3c(=O)cc(C(=O)OCCC(C)C)oc32)c1C]

In one aspect, the present invention provides a use and method of treatment or prophylaxis of lobular inflammation or non-alcoholic fatty liver disease in a subject with Repirinast or a pharmaceutically acceptable variation thereof. The non-alcoholic fatty liver disease may be NASH or NASH-HCC.

In an embodiment, the amount of Repirinast used is between 2 to 50 mg per kg of the subject per day. In a preferred embodiment, the amount of Repirinast used is between 5 to 10 mg per kg of the subject per day. In a further preferred embodiment, the amount of Repirinast used is about 10 mg per kg of the subject per day.

The Repirinast, or pharmaceutically acceptable variation thereof, may be administered to the subject orally, intravenously or in a manner known in the art. The Repirinast, or pharmaceutically acceptable variation thereof, may also be administered with one or more pharmaceutically acceptable excipients.

Use of Ifenprodil

Ifenprodil, 4-[2-(4-benzylpiperidin-1-yl)-1-hydroxypropyl]phenol, is known in the art as a selective NMDA receptor (glutamate) antagonist. The chemical structure is:

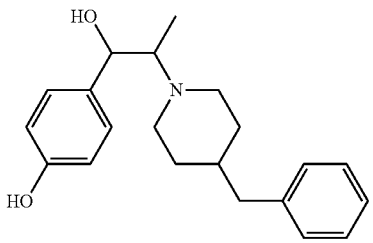 [SMILES: CC(C(O)c1ccc(O)cc1)N1CCC(Cc2ccccc2)CC1]

In some embodiments tested in the examples herein, Ifenprodil hemitartrate, 4-[2-(4-benzylpiperidin-1-ium-1-yl)-1-hydroxypropyl]phenol; 2,3,4-trihydroxy-4-oxobutanoate, having the following structure was used:

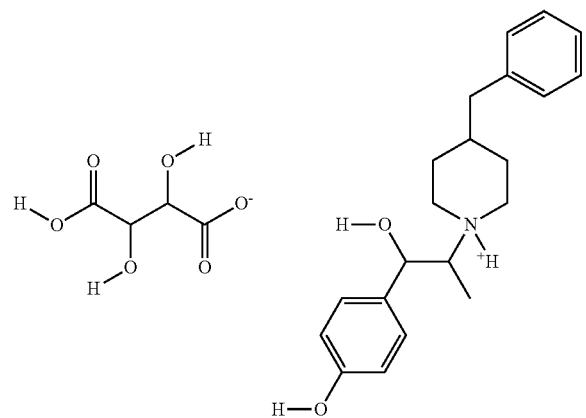

In one aspect, the present invention provides a use and method of treatment or prophylaxis of lobular inflammation or non-alcoholic fatty liver disease in a subject with Ifenprodil Hemitartrate or a pharmaceutically acceptable variation thereof. The non-alcoholic fatty liver disease may be NASH or NASH-HCC.

In an embodiment, the amount of Ifenoprodil used is between 0.1 and 5 mg per kg of the subject per day. In a preferred embodiment, the amount of Ifenoprodil used is between 0.5 to 3 mg per kg of the subject per day. In a further preferred embodiment, the amount of Ifenoprodil used is about 1 mg per kg of the subject per day.

The Ifenprodil Hemitartrate, or pharmaceutically acceptable variation thereof, may be administered to the subject orally, intravenously or in a manner known in the art. The Ifenprodil Hemitartrate, or pharmaceutically acceptable variation thereof, may also be administered with one or more pharmaceutically acceptable excipients.

Use of Bromantane

Bromantane, N-(4-Bromophenyl)adamantan-2-amine, is an atypical psychostimulant and anxiolytic drug of the adamantine family known in the art of treatment of neurasthenia. The chemical structure of Bromantane is:

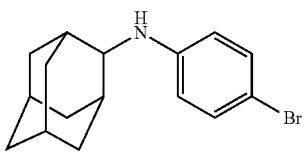 [SMILES: Brc1ccc(NC2C3CC4CC(C3)CC2C4)cc1]

In one aspect, the present invention provides a use and method of treatment or prophylaxis of lobular inflammation or non-alcoholic fatty liver disease in a subject with Bromantane or a pharmaceutically acceptable variation thereof. The non-alcoholic fatty liver disease may be NASH or NASH-HCC.

In an embodiment, the amount of Bromantane used is between 0.8 and 5 mg per kg of the subject per day. In a preferred embodiment, the amount of Bromantane used is between 1.7 to 3.3 mg per kg of the subject per day. In a further preferred embodiment, the amount of Bromantane used is about 1.7 mg per kg of the subject per day.

The Bromantane, or pharmaceutically acceptable variation thereof, may be administered to the subject orally, intravenously or in a manner known in the art. The Bromantane, or pharmaceutically acceptable variation thereof, may also be administered with one or more pharmaceutically acceptable excipients.

Use of Suplatast Tosylate

Suplatast Tosylate, (3-{[4-(3-ethoxy-2-hydroxypropoxy)phenyl]amino}-3-oxopropyl)(dimethyl)sulfonium 4-methylbenzenesulfonate, is a Th2 cytokine inhibitor known in the art as an antiallergic agent. The chemical structure of Suplatast Tosylate is:

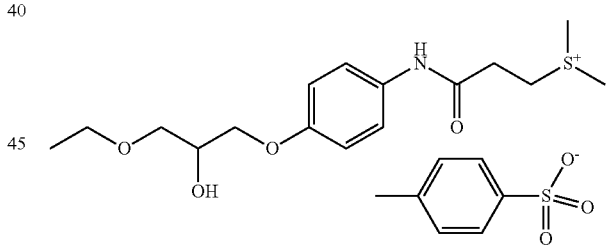

In one aspect, the present invention provides a use and method of treatment or prophylaxis of lobular inflammation or non-alcoholic fatty liver disease in a subject with Suplatast Tosylate or a pharmaceutically acceptable salt thereof. The non-alcoholic fatty liver disease may be NASH or NASH-HCC.

In an embodiment, the amount of Suplatast Tosylate used is between 1 to 10 mg per kg of the subject per day. In a preferred embodiment, the amount of Suplatast Tosylate used is between 2 to 8 mg per kg of the subject per day. In another preferred embodiment, the amount of Suplatast Tosylate used is between 4.5 to 5.4 mg per kg of the subject per day. In a yet further preferred embodiment, the amount of Suplatast Tosylate used is about 5 mg per kg of the subject per day.

The Suplatast Tosylate, or pharmaceutically acceptable salt thereof, may be administered to the subject orally, intravenously or in a manner known in the art. The Suplatast Tosylate, or pharmaceutically acceptable salt thereof, may also be administered with one or more pharmaceutically acceptable excipients.

Use of Actarit

Actarit, (4-Acetamidophenyl)acetic acid, is a disease-modifying antirheumatic drug known in the art for treatment of rheumatoid arthritis. The chemical structure of Actarit is:

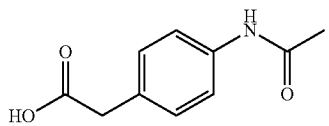

In one aspect, the present invention provides a use and method of treatment or prophylaxis of lobular inflammation or non-alcoholic fatty liver disease in a subject with Actarit or a pharmaceutically acceptable variation thereof. The non-alcoholic fatty liver disease may be NASH or NASH-HCC.

In an embodiment, the amount of Actarit used is between 3.75 to 6.25 mg per kg of the subject per day. In a preferred embodiment, the amount of Actarit used is between 4.16 to 5.83 mg per kg of the subject per day. In another preferred embodiment, the amount of Actarit used is between 4.58 to 5.42 mg per kg of the subject per day. In a yet further preferred embodiment, the amount of Actarit used is about 5 mg per kg of the subject per day.

The Actarit, or pharmaceutically acceptable variation thereof, may be administered to the subject orally, intravenously or in a manner known in the art. The Actarit, or pharmaceutically acceptable variation thereof, may also be administered with one or more pharmaceutically acceptable excipients.

Use of Lobenzarit

Lobenzarit, 2-[(2-Carboxyphenyl)amino]-4-chlorobenzoic acid, is an immunomodulator known in the art for treatment of arthritis. The chemical structure of Lobenzarit is:

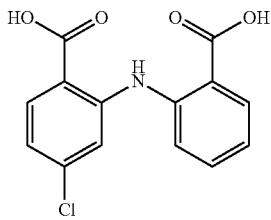 [SMILES: O=C(O)c1ccccc1Nc1cc(Cl)ccc1C(=O)O]

In one aspect, the present invention provides a use and method of treatment or prophylaxis of lobular inflammation or non-alcoholic fatty liver disease in a subject with Lobenzarit or a pharmaceutically acceptable variation thereof. The non-alcoholic fatty liver disease may be NASH or NASH-HCC.

In an embodiment, the amount of Lobenzarit used is between 1 to 10 mg per kg of the subject per day. In a preferred embodiment, the amount of Lobenzarit used is between 2 to 7 mg per kg of the subject per day. In another preferred embodiment, the amount of Lobenzarit used is between 3 to 5 mg per kg of the subject per day. In a yet further preferred embodiment, the amount of Lobenzarit used is about 4 mg per kg of the subject per day.

The Lobenzarit, or pharmaceutically acceptable variation thereof, may be administered to the subject orally, intravenously or in a manner known in the art. The Lobenzarit, or pharmaceutically acceptable variation thereof, may also be administered with one or more pharmaceutically acceptable excipients.

Use of Irsogladine

Irsogladine, 6-(2,5-Dichlorophenyl)-1,3,5-triazine-2,4-diamine, is a phosphodiesterase inhibitor known in the art as a mucosal protective drug used in the treatment of peptic ulcer disease and acute gastritis. The chemical structure of Irsogladine is:

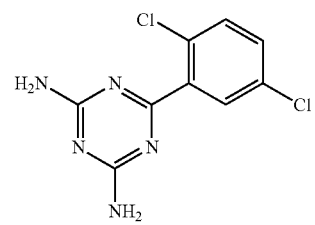 [SMILES: Nc1nc(N)nc(-c2cc(Cl)ccc2Cl)n1]

In one aspect, the present invention provides a use and method of treatment or prophylaxis of lobular inflammation or non-alcoholic fatty liver disease in a subject with Irsogladine or a pharmaceutically acceptable variation thereof. The non-alcoholic fatty liver disease may be NASH or NASH-HCC.

In an embodiment, the amount of Irsogladine used is between 0.0416 to 0.125 mg per kg of the subject per day. In a preferred embodiment, the amount of Irsogladine used is between 0.066 to 0.1 mg per kg of the subject per day. In a further preferred embodiment, the amount of Irsogladine used is about 0.08 mg per kg of the subject per day. In a further preferred embodiment, the amount of Irsogladine used is about 0.07 mg per kg of the subject per day.

The Irsogladine, or pharmaceutically acceptable variation thereof, may be administered to the subject orally, intravenously or in a manner known in the art. The Irsogladine, or pharmaceutically acceptable variation thereof, may also be administered with one or more pharmaceutically acceptable excipients.

Use of Istradefylline

Istradefylline, 8-[(E)-2-(3,4-dimethoxyphenyl)vinyl]-1,3-diethyl-7-methyl-3,7-dihydro-1H-purine-2,6-dione, is a selective A2A receptor antagonist known in the art for treatment of dyskinesia in Parkinson's disease. The chemical structure of Istradefylline is:

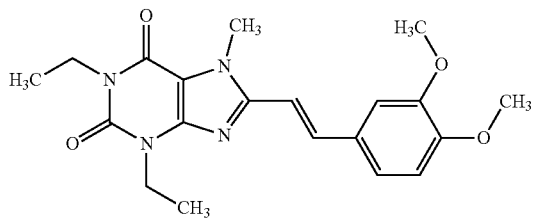 [SMILES: CCn1c(=O)c2c(nc(/C=C/c3ccc(OC)c(OC)c3)n2C)n(CC)c1=O]

In one aspect, the present invention provides a use and method of treatment or prophylaxis of lobular inflammation or non-alcoholic fatty liver disease in a subject with Istradefylline or a pharmaceutically acceptable variation thereof. The non-alcoholic fatty liver disease may be NASH or NASH-HCC.

In an embodiment, the amount of Istradefylline used is between 0.1 to 5 mg per kg of the subject per day. In a preferred embodiment, the amount of Istradefylline used is between 0.3 to 1.3 mg per kg of the subject per day. In a further preferred embodiment, the amount of Istradefylline used is about 1.3 mg per kg of the subject per day.

The Istradefylline, or pharmaceutically acceptable variation thereof, may be administered to the subject orally, intravenously or in a manner known in the art. The Istradefylline, or pharmaceutically acceptable variation thereof, may also be administered with one or more pharmaceutically acceptable excipients.

Use of Trapidil

Trapidil, N,N-Diethyl-5-methyl-[1,2,4]triazolo[1,5-a]pyrimidin-7-amine, is known in the art as a vasodilator, antiplatelet drug, and platelet-derived growth factor antagonist. The chemical structure of Trapidil is:

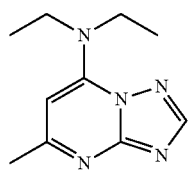

In one aspect, the present invention provides a use and method of treatment or prophylaxis of lobular inflammation or non-alcoholic fatty liver disease in a subject with Trapidil or a pharmaceutically acceptable variation thereof. The non-alcoholic fatty liver disease may be NASH or NASH-HCC.

In an embodiment, the amount of Trapidil used is between 4.16 to 5.83 mg per kg of the subject per day. In a preferred embodiment, the amount of Trapidil used is between 4.58 to 5.41 mg per kg of the subject per day. In a further preferred embodiment, the amount of Trapidil used is about 5 mg per kg of the subject per day. In yet another embodiment, prior to the use of 5 mg per kg of Trapidil on the subject, a single dose of 10 mg/kg of Trapidil was used on the subject.

The Trapidil, or pharmaceutically acceptable variation thereof, may be administered to the subject orally, intravenously or in a manner known in the art. The Trapidil, or pharmaceutically acceptable variation thereof, may also be administered with one or more pharmaceutically acceptable excipients.

Use of Bemithyl

Bemithyl, 2-Ethylsulfanyl-1H-benzoimidazole, is known in the art as a synthetic actoprotector, antioxidant, and antimutagenic, and is often used to increase physical performance. The chemical structure of Bemithyl is:

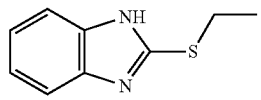

In one aspect, the present invention provides a use and method of treatment or prophylaxis of lobular inflammation or non-alcoholic fatty liver disease in a subject with Bemithyl or a pharmaceutically acceptable variation thereof. The non-alcoholic fatty liver disease may be NASH or NASH-HCC.

In an embodiment, the amount of Bemithyl used is between 0.5 to 30 mg per kg of the subject per day. In a preferred embodiment, the amount of Bemithyl used is between 1 to 25 mg per kg of the subject per day. In a further preferred embodiment, the amount of Bemithyl used is between 5 to 20 mg per kg of the subject per day. In a yet further preferred embodiment, the amount of Bemithyl used is about 8 mg per kg of the subject per day. In a still further preferred embodiment, the amount of Bemithyl used is about 17 mg per kg of the subject per day.

The Bemithyl, or pharmaceutically acceptable variation thereof, may be administered to the subject orally, intravenously or in a manner known in the art. The Bemithyl, or pharmaceutically acceptable variation thereof, may also be administered with one or more pharmaceutically acceptable excipients.

Use in Combination

In another aspect, the present invention provides a use and method of treatment or prophylaxis of NASH or NASH-HCC in a subject with one or more of Cepharanthine, Repirinast, Ifenoprodil Hemitartrate, Bromantane, Suplatast Tosylate, Actarit, Lobenzarit, Irsogladine, Istradefylline and Trapidil in combination. In another aspect, the present invention provides a use and method of treatment or prophylaxis of NASH or NASH-HCC in a subject with one or more of Cepharanthine, Repirinast, Ifenoprodil Hemitartrate, Bromantane, Suplatast Tosylate, Actarit, Lobenzarit, Irsogladine, Istradefylline and Trapidil in combination with one or more of a cholesterol lowering drug, a diabetes drug, an antihypertension drug, or Vitamin E.

Examples of cholesterol lowering drugs for use in combinations include Atorvastatin (Lipitor), Fluvastatin (Lescol), Lovastatin, Pitavastatin (Livalo), Pravastatin (Pravachol), Rosuvastatin calcium (Crestor), Simvastatin (Zocor) and niacin, Alirocumab (Praluent), Evolocumab (Repatha), Alirocumab (Praluent), and Evolocumab (Repatha). Examples of diabetes drugs for use in combinations include insulin. Examples of antihypertension drugs for use in combinations include antihypertensives, calcium channel blockers, ACE inhibitors angiotensin II receptor blockers, diuretics, and beta blockers. Examples of known angiotensin II receptor antagonists include both angiotensin I receptor subtype antagonists and angiotensin II receptor subtype antagonists. Suitable angiotensin II receptor antagonists include losartan and valsartan. Suitable calcium channel blockers include, for example, verapamil, diltiazem, nicardipine, nifedipine, amlodipine, felodipine, nimodipine, and bepridil. Diuretics include, for example, furosemide, diuril, amiloride, and hydrodiuril. Losartan, candesartan, telmisartan, valsartan, olmesartan, irbesartan, and the like can be used as a hypotensive agent.

The term "effective amount" used herein refers to the amount of an active ingredient sufficient to confer a desired prophylactic or therapeutic effect in a treated subject. In one aspect, an effective amount for inhibiting or alleviating hepatic steatosis, lobular inflammation, hepatocellular ballooning or NASH-derived HCC improves or reduces one or more symptoms, conditions or progression thereof. In some embodiments, the symptoms, conditions or progression are determined and evaluated using methods known in the art that measure various disease progress-related indexes, for example by analyzing liver sections via immunohistochemical staining.

In some embodiments, the effective amount is determined by persons skilled in the art evaluating, for example, the administration route and frequency, body weight and species of the subject receiving the pharmacologic compound. In some embodiments, an effective amount of the pharmacologic compound is formulated with a pharmaceutically acceptable vehicle and administered to the subject.

The term "pharmaceutically acceptable" used herein means that the vehicle is known in the art as compatible with the pharmacologic compound while also being safe to the subject receiving the treatment. In some embodiments, the pharmaceutically acceptable vehicle is determined by persons skilled in the art evaluating, for example, the solubility of the pharmacologic compound in said vehicle.

Exemplary embodiments of the present invention are further described with reference to the following examples, which are intended to be illustrative and not limiting in nature. In the first study, a therapeutically effective amount of 10 pharmacologic compounds was administered. In the second study, a therapeutically effective amount of 5 pharmacologic compounds were administered.

Example 1

Materials and Methods

Male newborn C57BL/6 mice were used. All mice were born from pathogen-free 14 day-pregnant mice obtained from Japan SLC, Inc. (Hamamatsu, Japan) prior to the start of the study.

The murine STAM™ model of NASH-HCC was performed according to previously described methods known in the art (Takakura et al, Characterization of non-alcoholic steatohepatitis, Anticancer Res, 34(9):4849-55 (2014); Fujii et al, (2013)). NASH was induced in male mice by a single subcutaneous injection of 200 µg of streptozotocin (STZ, Sigma, Mo., USA) at 2 days after birth and continuous feeding after 4 weeks of age (day 28±2) with a high fat diet (CLEA Japan Inc, Tokyo, Japan) given ad libitum.

Following induction of NASH, the mice were randomized into 12 individual study groups of 8 mice each at 6 weeks of age (day 42±2) based on body weight, the day before the start of treatment.

One day following randomization, the mice were administered a once-daily oral treatment from 6 weeks of age plus one day (day 43±2, treatment Day 1) to 9 weeks of age (hereinafter known as the "treatment period"). The mice in 11 of the 12 study groups (hereafter known as "treatment groups") were treated individually with a distinct pharmacologic compound formulated with a pharmaceutically acceptable vehicle. The pharmacologic compound that each of these 11 groups received were either 1 of 10 test agents or Telmisartan as the positive control. The pharmaceutically acceptable vehicle in all groups was 0.5% carboxymethyl cellulose (CMC). The mice in the remaining study group (hereafter known as the "vehicle control group") were treated individually with the same pharmaceutically acceptable vehicle with no active ingredient. Individual body weight was measured daily during the treatment period. Survival, clinical signs and behavior of mice were also monitored daily.

TABLE 1

| | Groups | Once daily oral dosing mg/kg |
|---|---|---|
| 1 | Normal (no NASH) | N/A |
| 2 | Telmisartan (+) | 10 |
| 3 | Vehicle (−) | N/A |
| 4 | Cepharanthine | 12 |
| 5 | Repirinast | 60 |
| 6 | Ifenoprodil Hemitartrate | 30 |
| 7 | Bromantane | 20 |
| 8 | Suplatast Tosylate | 60 |

TABLE 1-continued

| | Groups | Once daily oral dosing mg/kg |
|---|---|---|
| 9 | Actarit | 60 |
| 10 | Lobenzarit | 48 |
| 11 | Irsogladine | 1 |
| 12 | Istradefylline | 18 |
| 13 | Trapadil | 60 |

In each case, a volume of 10 mL/kg of 0.5% CMC was administered orally with (or without) the active ingredient as noted in Table 1 from 6 to 9 weeks of age until sacrifice. One exception being Trapadil, which was administered orally with one dosing of 120 mg/kg on Day 0 and then at the daily dose of 60 mg/kg starting on treatment Day 1. All mice were then sacrificed at 9 weeks of age. Blood samples were collected from all mice and the liver from each mouse was removed for analysis.

The dose selected for the animal studies was determined by taking the maximum known human daily dose, dividing by the average weight of an adult (~60-70 kg) to get a human mg/kg dose. Then that number was multiplied by 12 to convert to a mouse dose based on conventional dosing tables. See Nair and Jacob, J Basic Clin Pharm March 2016-May 2016, 7(2):27-31.

The following measurements and assessments were taken for each mouse.

Body weight: The body weight of all mice were measured daily throughout the treatment period.

Blood Sample Collection and Biochemical Analysis: Blood was collected from all sacrificed mice and frozen for further analyses or shipping.

Plasma Alanine Aminotransferase (ALT): The plasma from each blood sample was analyzed by FUJI DRI CHEM (Fujifilm, Japan) for alanine aminotransferase (ALT) as an indicator of liver function and disease progression.

Liver Sample Collection, Biochemical Analysis, and Histological Analysis: The liver was removed from all sacrificed mice and frozen for further analyses or shipping.

Liver Weight: Following removal, the livers from all sacrificed mice were weighed in grams.

Liver Histopathology: The removed livers were fixed in formalin and embedded in paraffin, and cross sections (4 µm) were then prepared.

Assessment of Steatohepatitis: Liver cross-sections were subjected to hematoxylin and eosin (H&E) staining using standard techniques for histological assessment of hepatic steatosis, lobular inflammation and hepatocellular ballooning. The level of steatohepatitis severity in each liver cross-section was indicated by NAFLD Activity Scores of: 0 (normal), 1-2 (NAFLD), 3-4 (borderline) or at least 5 (NASH) in 3 randomly selected fields of H&E-stained liver cross-sections of 4 µm thickness at ×50 magnification for evaluation of steatosis and ×200 magnification each for evaluation of inflammation and evaluation of ballooning. The NAFLD Activity Score is the unweighted sum of the following: 1) hepatic steatosis score (0-3); 2) lobular inflammation score (0-2); 3) hepatocellular ballooning score (0-2).

The liver cross-sections of the Vehicle group, and the Bromantane, Istradefylline, and Telmisartan treated groups were also subjected to Sirius-red staining using standard techniques for histological estimation of the percentage of fibrosis area. For quantitative analysis of fibrosis area, bright field images of Sirius red-stained sections were captured around the central vein using a digital camera (DFC295; Leica, Germany) at 200-fold magnification, and the positive areas in 5 fields/section were measured using ImageJ software (National Institute of Health, USA).

Statistical Analysis

Values are arithmetic means. Comparison between the study group and positive control group was performed using a two-tailed, heteroscedastic (two-sample unequal variance) Student's T-Test. A P-value of <0.05 was considered statistically significant following a Bonferroni post-hoc statistical correction analysis for multiple groups (Bonferroni Multiple Comparison Test). In this case, the correction factor was 12, corresponding to the number of study groups. Following the usual convention, the P-value classification and statistical significance levels chosen are shown in Table 2 alongside their corresponding classification scores.

TABLE 2

P-Value Classification: Statistical Significance Levels

| P-Value | Statistical | Classification |
|---|---|---|
| P ≥ 0.05 | Not Significant | NS |
| 0.01 ≤ P < 0.05 | Significant | * |
| 0.001 ≤ P < 0.01 | Very Significant | ** |
| P < 0.001 | Extremely | *** |

Results

Liver Function Evaluation: Liver function and disease progression was evaluated by Plasma ALT as previously described. Results are summarized in FIG. 1.

Steatohepatitis Evaluation: Steatohepatitis and disease progression was evaluated by H&E-staining of liver cross-sections as previously described. Representative photomicrographs of HE-stained liver sections for each of the 12 study groups are shown in FIGS. 2a-2d.

The NAFLD Activity Score of each study group consisted of the NAFLD Activity Score average of all mice in each study group. Scores were determined based on the steatosis score, lobular inflammation score and hepatocellular ballooning score for each animal. Results are summarized in FIGS. 3-6.

Figure 7:
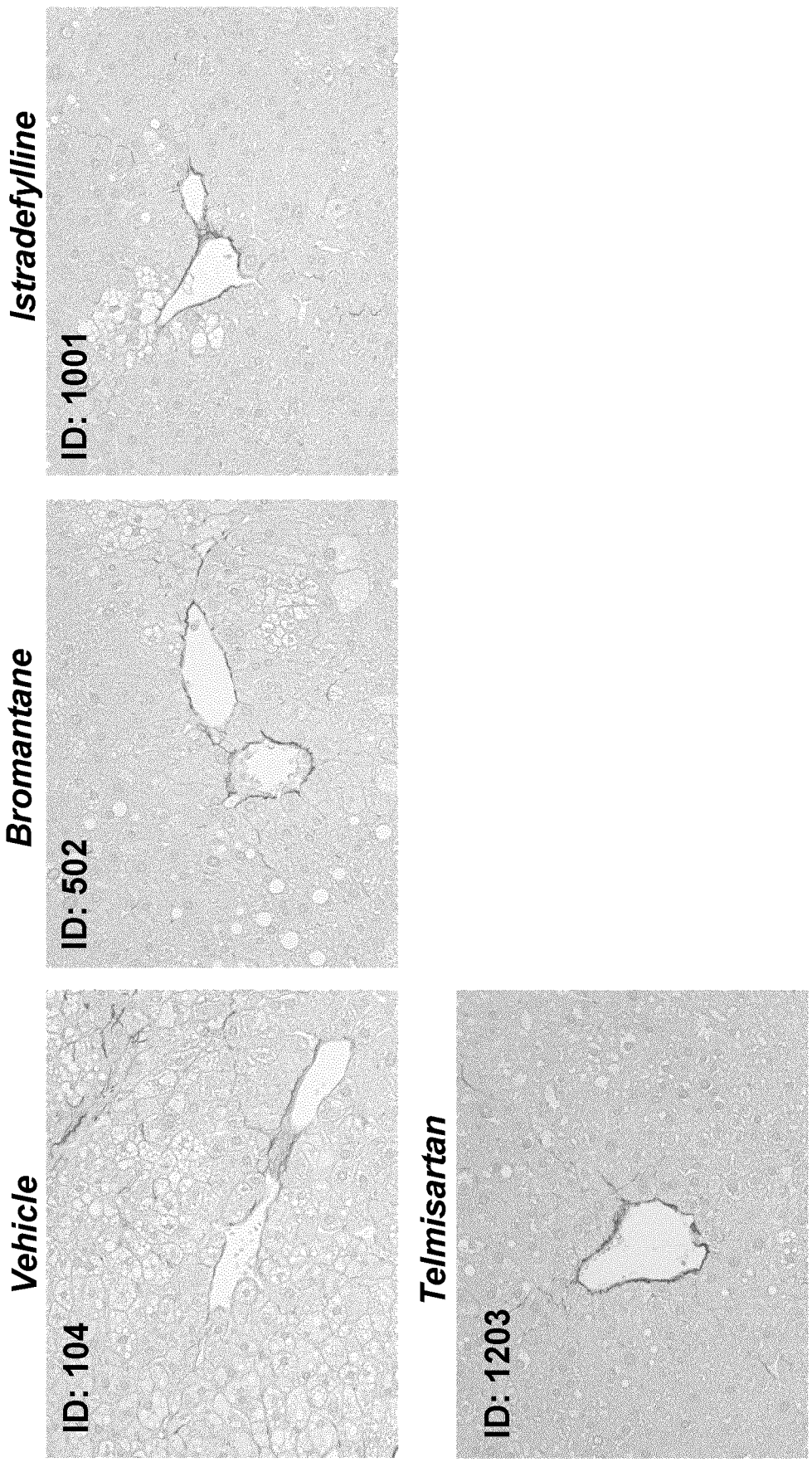
FIG. 7 shows representative photomicrographs of Sirius red-stained liver sections for study groups of C57BL/6 mice consisting of the "Vehicle" control group and the Bromantane and Istradefylline treatment groups including the positive control treatment group, Telmisartan. The panels are taken at ×200 magnification. The identity of each study group is listed above the upper panel in each pair of panels.
Figure 8:
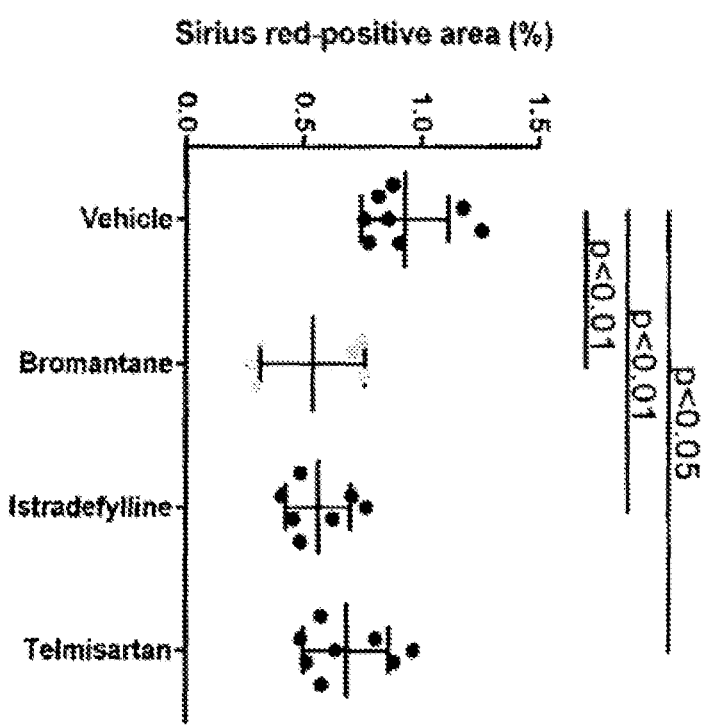
FIG. 8 shows the Sirius red-positive area for study groups of C57BL/6 mice consisting of the "Vehicle" control group and the Bromantane and Istradefylline treatment groups including the positive control treatment group, Telmisartan. Mean is indicated±SD as determined using the Bonferroni multiple comparison test.

Steatohepatitis and disease progression was also evaluated by Sirius-red staining of liver cross-sections as previously described. Representative photomicrographs of Sirius red-stained liver sections for Vehicle, Bromantane, Istradefylline, and Telmisartan study groups are shown in FIG. 7. Results are shown in FIG. 8.

Statistically significant reductions in NAFLD activity score relative to Vehicle control were observed for the Bromantane and Istradefylline treatment groups, as well as for the Telmisartan positive control. Statistically significant reductions in hepatocellular ballooning score relative to Vehicle control were observed for the Bromantane, Irsogladine and Istradefylline treatment groups.

The Bromantane and Istradefylline groups showed significant decreases in the fibrosis area (Sirius red-positive area) compared with the Vehicle group. The fibrosis area in the Telmisartan group tended to decrease compared with the Vehicle group. Liver sections from the Vehicle group showed increased collagen deposition in the pericentral region of liver lobule.

The statistically significant and clinically relevant composite reduction in NAFLD Activity Scores, particularly for Bromantane and Istradefylline, suggest these compounds could be useful in preventing and/or treating NASH and its sequelae.

Example 2

Materials and Methods

As before, male newborn C57BL/6 mice were used. All mice were born from pathogen-free 14 day-pregnant mice obtained from Japan SLC, Inc. (Hamamatsu, Japan) prior to the start of the study.

The murine STAM™ model of NASH-HCC was performed according to previously described methods known in the art (Takakura et al, Characterization of non-alcoholic steatohepatitis, Anticancer Res, 34(9):4849-55 (2014); Fujii et al, (2013)). NASH was induced in male mice by a single subcutaneous injection of 200 µg of streptozotocin (STZ, Sigma, Mo., USA) at 2 days after birth and continuous feeding after 4 weeks of age (day 28±2) with a high fat diet (CLEA Japan Inc, Tokyo, Japan) given ad libitum.

Following induction of NASH, the mice were randomized into 7 individual study groups of 8 mice each at 6 weeks of age (day 42±2) based on their body weight, the day before the start of treatment.

One day following randomization, the mice were administered a once-daily oral treatment from 6 weeks of age plus one day (day 43±2, treatment Day 1) to 9 weeks of age. The mice in 6 of the 7 study groups were treated individually with a therapeutic amount of a pharmacologic compound formulated with a pharmaceutically acceptable vehicle. The pharmacologic compound that each of these 6 groups received were either 1 of 4 test agents or Telmisartan as the positive control. The pharmaceutically acceptable vehicle in all groups was 0.5% CMC. The mice in the remaining study group, the vehicle control group, were treated individually with the same pharmaceutically acceptable vehicle with no active ingredient. Individual body weight was measured daily during the treatment period. Survival, clinical signs and behavior of mice were also monitored daily.

TABLE 3

| | Groups | Once daily oral dosing mg/kg |
|---|---|---|
| 1 | Normal (no NASH) | N/A |
| 2 | Telmisartan (+) | 10 |
| 3 | Vehicle (−) | N/A |
| 4 | Bromantane | 20 |
| 5 | Bromantane | 40 |
| 6 | Bemithyl | 200 |
| 7 | Cenicriviroc | 30 |

In each case, a volume of 10 mL/kg of 0.5% CMC was administered orally with (or without) the active ingredient as noted in Table 3 from 6 to 9 weeks of age. All mice were then sacrificed at 9 weeks of age. Blood samples were collected from all mice and the liver from each mouse was removed for analysis.

The dose selected for the animal studies was determined by taking the maximum known human daily dose, dividing by the average weight of an adult (~60-70 kg) to get a human mg/kg dose. Then that number was multiplied by 12 to convert to a mouse dose based on conventional dosing tables. See Nair and Jacob, *J Basic Clin Pharm* March 2016-May 2016, 7(2):27-31.

The following measurements and assessments were taken for each mouse.

Body weight: The body weight of all mice was measured daily throughout the treatment period.

Blood Sample Collection and Biochemical Analysis: Blood was collected from all sacrificed mice and frozen for further analyses or shipping.

Plasma Alanine Aminotransferase (ALT): The plasma from each blood sample was analyzed by FUJI DRI CHEM (Fujifilm, Japan) for alanine aminotransferase (ALT) as an indicator of liver function and disease progression.

Liver Sample Collection, Biochemical Analysis, and Histological Analysis: The liver was removed from all sacrificed mice and frozen for further analyses or shipping. Following removal, the livers from all sacrificed mice were weighed in grams.

Liver Histopathology: The removed livers were fixed in formalin and embedded in paraffin, and cross sections (4 μm) were then prepared.

Assessment of Steatohepatitis: Liver cross-sections were subjected to hematoxylin and eosin (H&E) staining using standard techniques for histological assessment of hepatic steatosis, lobular inflammation and hepatocellular ballooning. The level of steatohepatitis severity in each liver cross-section was indicated by NAFLD Activity Scores of: 0 (normal), 1-2 (NAFLD), 3-4 (borderline) or at least 5 (NASH) in 3 randomly selected fields of H&E-stained liver cross-sections of 4 μm thickness at ×50 magnification for evaluation of steatosis and ×200 magnification each for evaluation of inflammation and evaluation of ballooning. The NAFLD Activity Score is the unweighted sum of the following: 1) hepatic steatosis score (0-3); 2) lobular inflammation score (0-2); 3) hepatocellular ballooning score (0-2).

The liver cross-sections of the treated groups were also subjected to Sirius-red staining using standard techniques for histological estimation of the percentage of fibrosis area. For quantitative analysis of fibrosis area, bright field images of Sirius red-stained sections were captured around the central vein using a digital camera (DFC295; Leica, Germany) at 200-fold magnification, and the positive areas in 5 fields/section were measured using ImageJ software (National Institute of Health, USA).

Statistical Analysis

Values are arithmetic means. Comparison between the study group and positive control group was performed using a two-tailed, heteroscedastic (two-sample unequal variance) Student's T-Test. A P-value of <0.05 was considered statistically significant following a Bonferroni post-hoc statistical correction analysis for multiple groups (Bonferroni Multiple Comparison Test). In this case, the correction factor was 7, corresponding to the number of study groups. Following the usual convention, the P-value classification and statistical significance levels chosen are shown in Table 2 (above) alongside their corresponding classification scores.

Results

Figure 9:
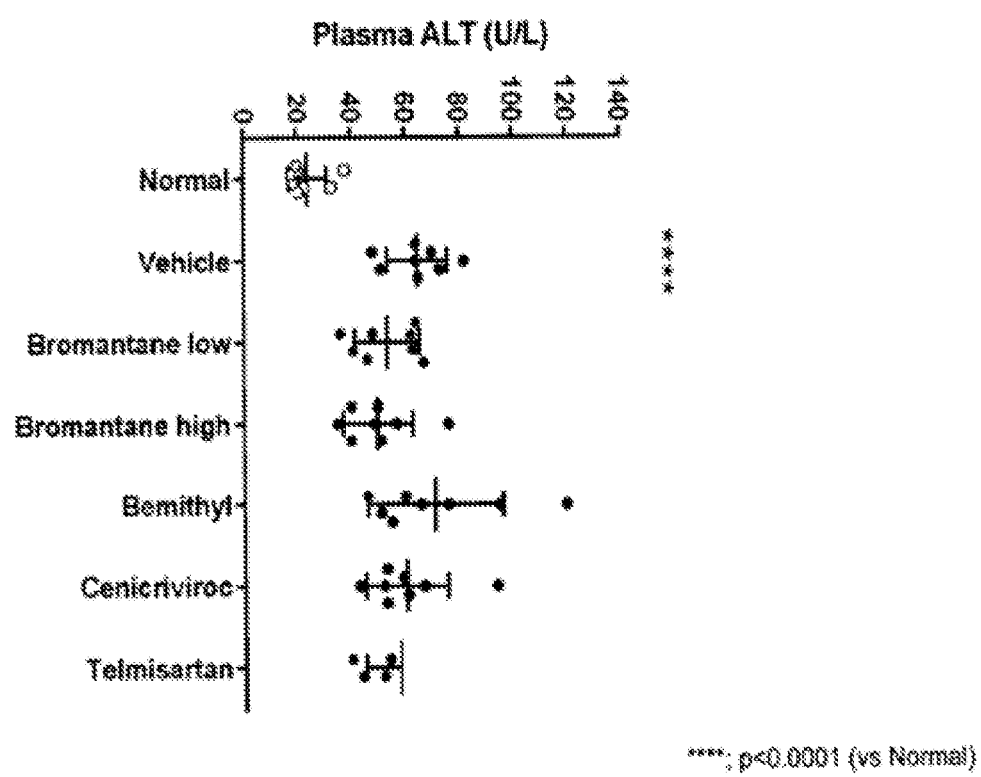
FIG. 9 shows an evaluation of liver function and disease progression consisting of the Plasma Alanine Aminotransferases (ALT) in units/L for 7 study groups in a second study of C57BL/6 mice consisting of the Normal (no NASH) group, the "Vehicle" control group and 5 treatment groups including the positive control treatment group, Telmisartan. Mean is indicated±SD as determined using the Bonferroni multiple comparison test.

Liver Function Evaluation: Liver function and disease progression was evaluated by Plasma ALT as previously described. Results are summarized in FIG. 9.

Figure 10A:
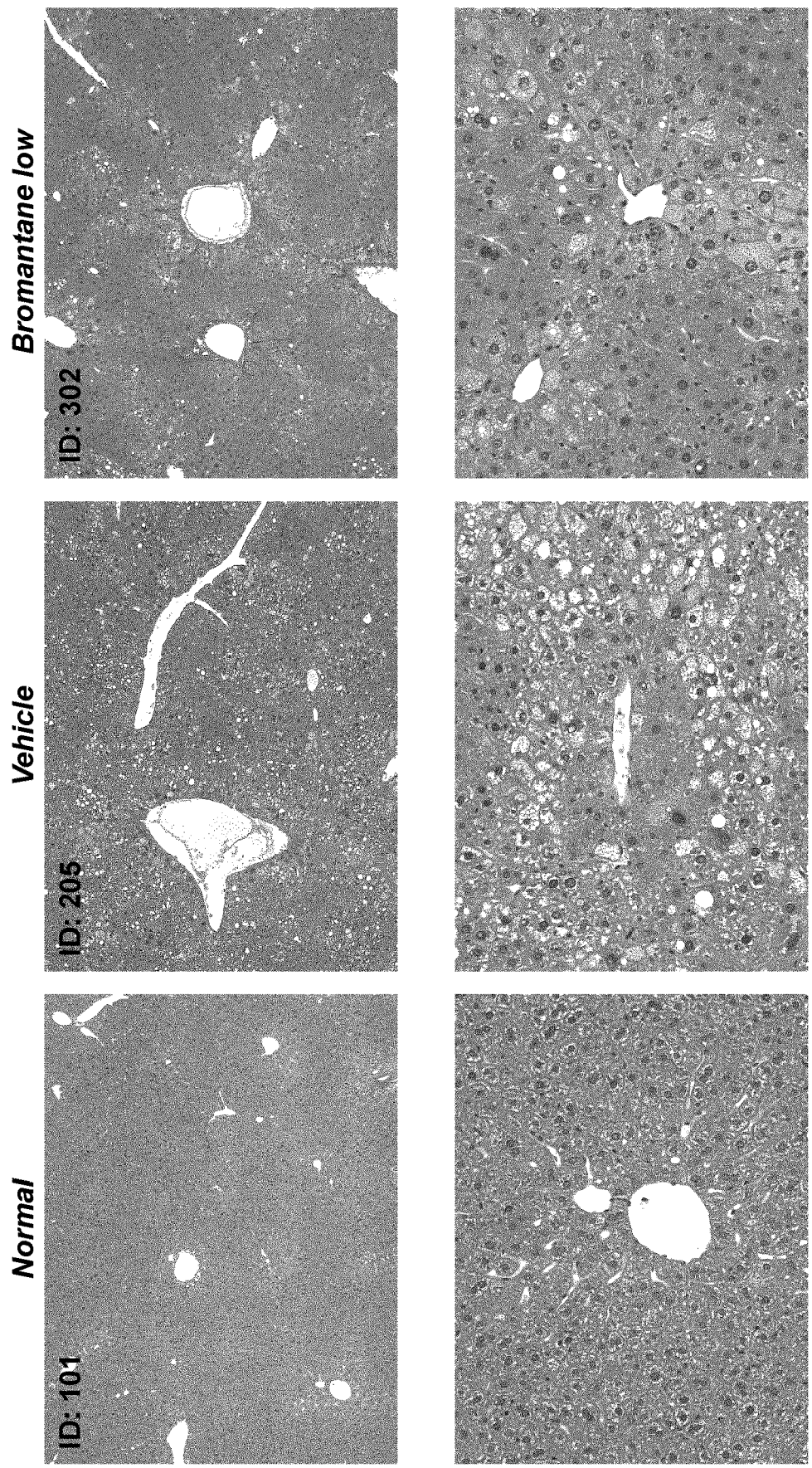
Figure 10C:
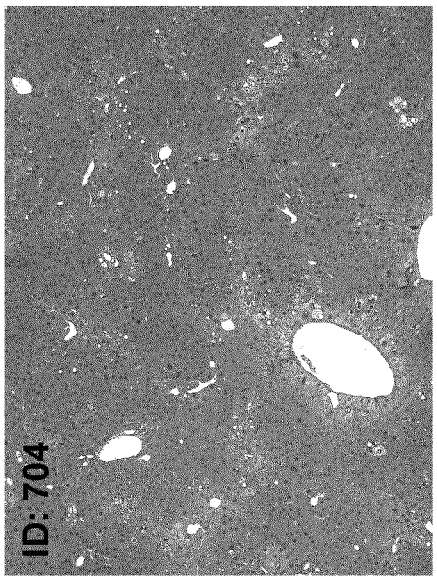
Figure 10C:
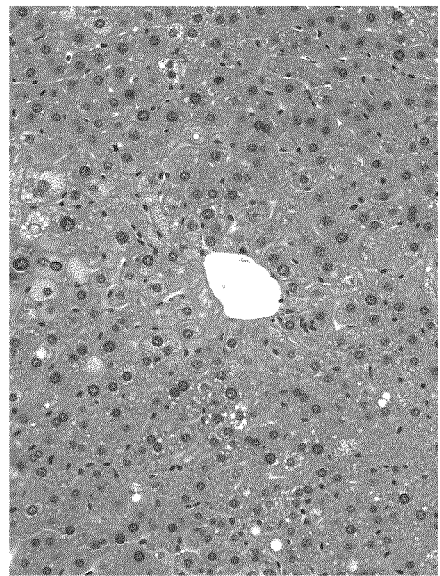
Figure 11:
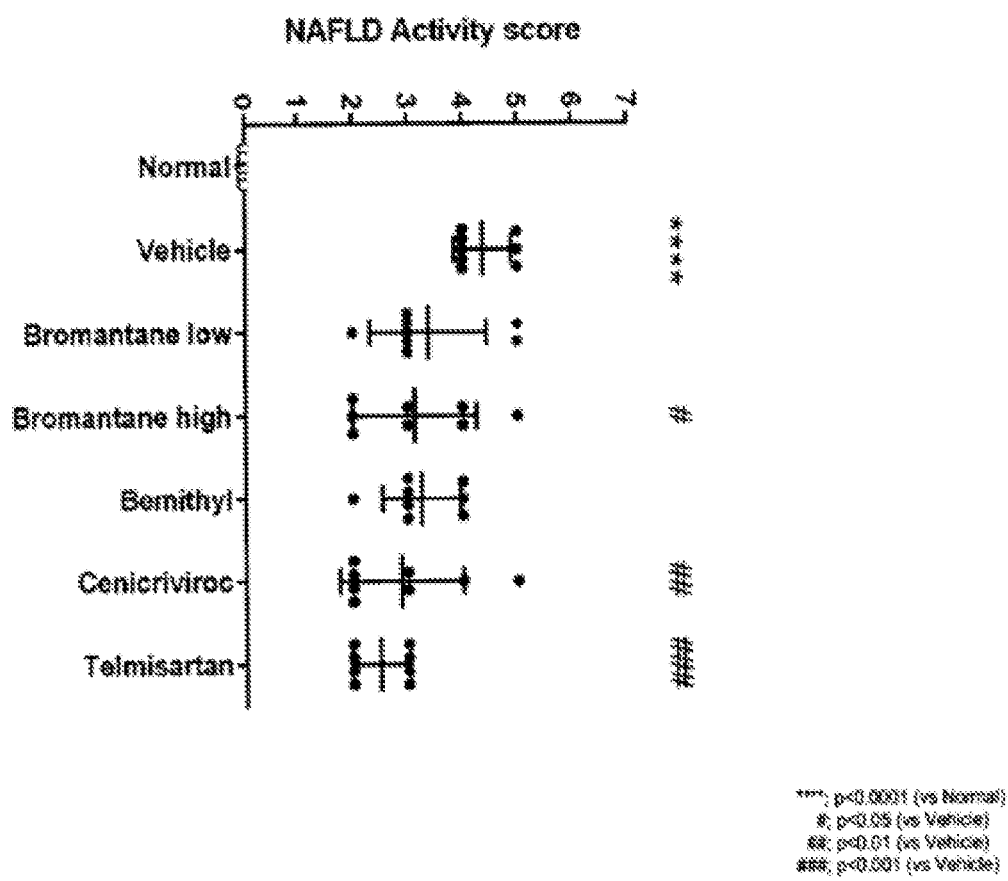
FIG. 11 shows the NAFLD activity score for each of the 7 study groups of C57BL/6 mice consisting of the Normal (no NASH) group, the "Vehicle" control group and 5 treatment groups including the positive control treatment group, Telmisartan. Mean is indicated±SD as determined using the Bonferroni multiple comparison test.
Figure 12:
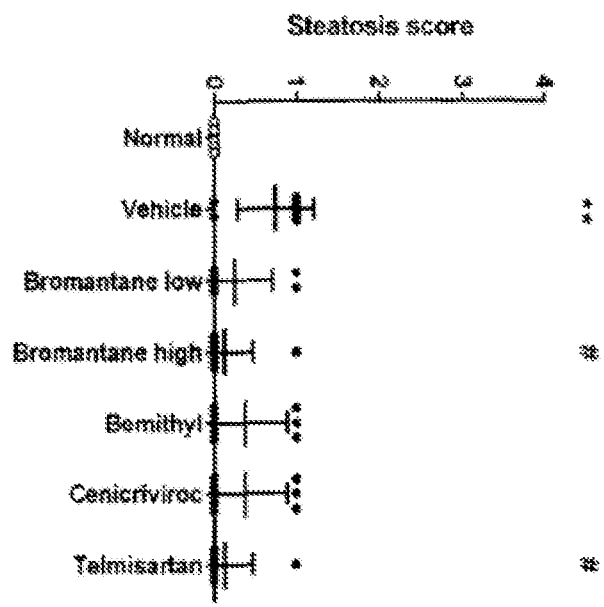
FIG. 12 shows the steatosis score for each of the 7 study groups of C57BL/6 mice consisting of the Normal (no NASH) group, the "Vehicle" control group and the 5 treatment groups including the positive control treatment group, Telmisartan. Mean is indicated±SD as determined using the Bonferroni multiple comparison test.
Figure 13:
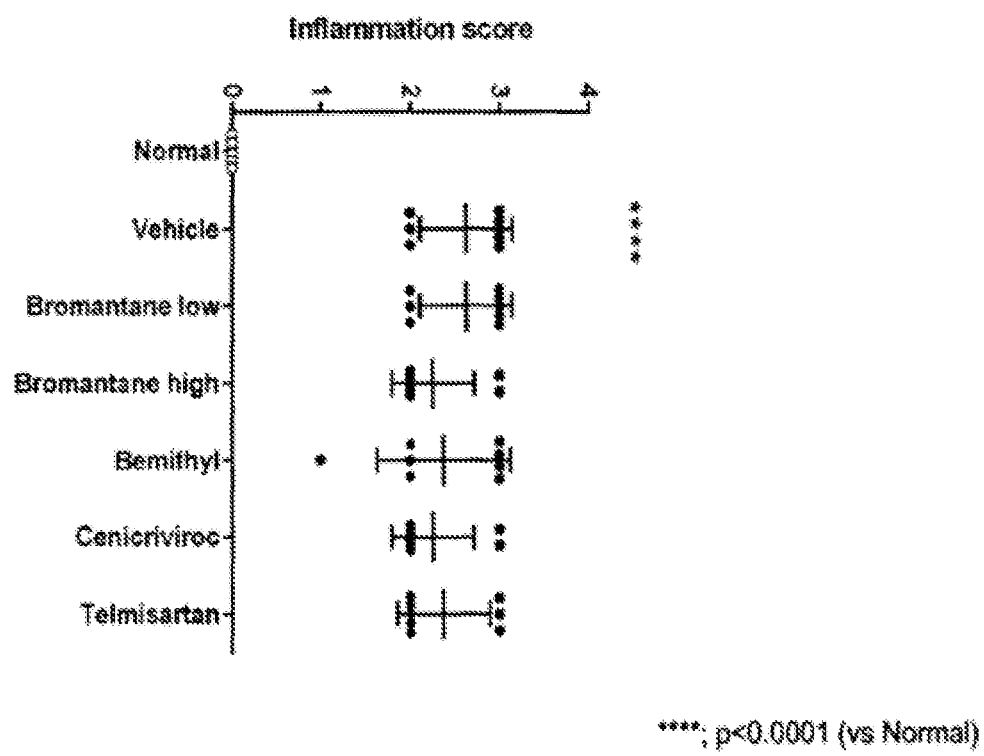
FIG. 13 shows the lobular inflammation score for each of the 7 study groups of C57BL/6 mice consisting of the Normal (no NASH) group, the "Vehicle" control group and the 5 treatment groups including the positive control treatment group, Telmisartan. Mean is indicated±SD as determined using the Bonferroni multiple comparison test.
Figure 14:
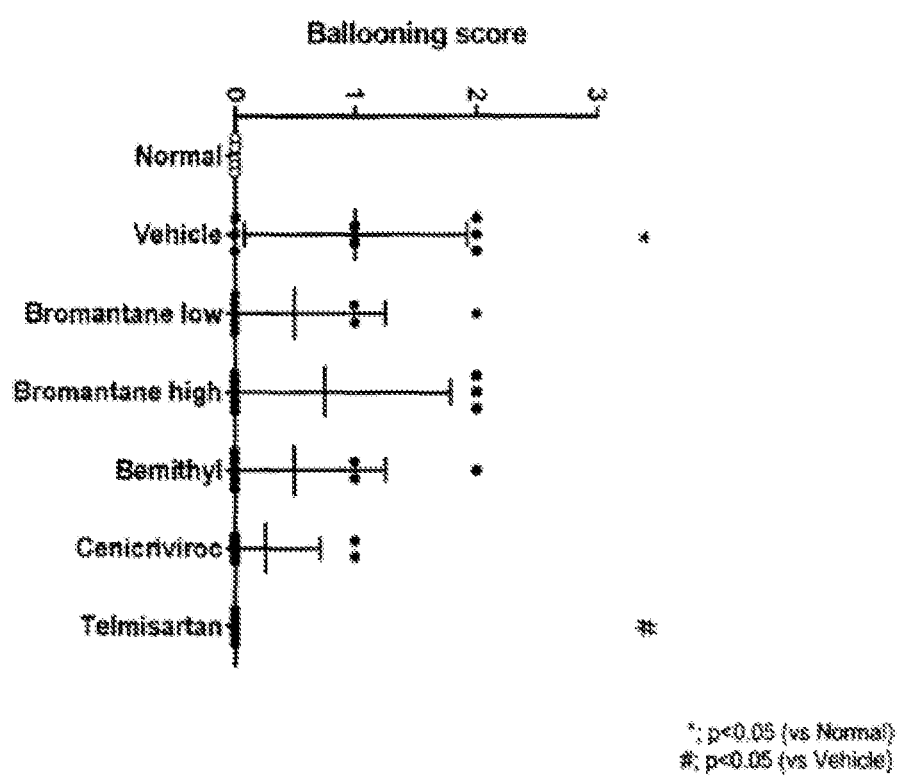
FIG. 14 shows the hepatocellular ballooning score for each of the 7 study groups of C57BL/6 mice consisting of the Normal (no NASH) group, the "Vehicle" control group and the 5 treatment groups including the positive control treatment group, Telmisartan. Mean is indicated±SD as determined using the Bonferroni multiple comparison test.
Figure 15A:
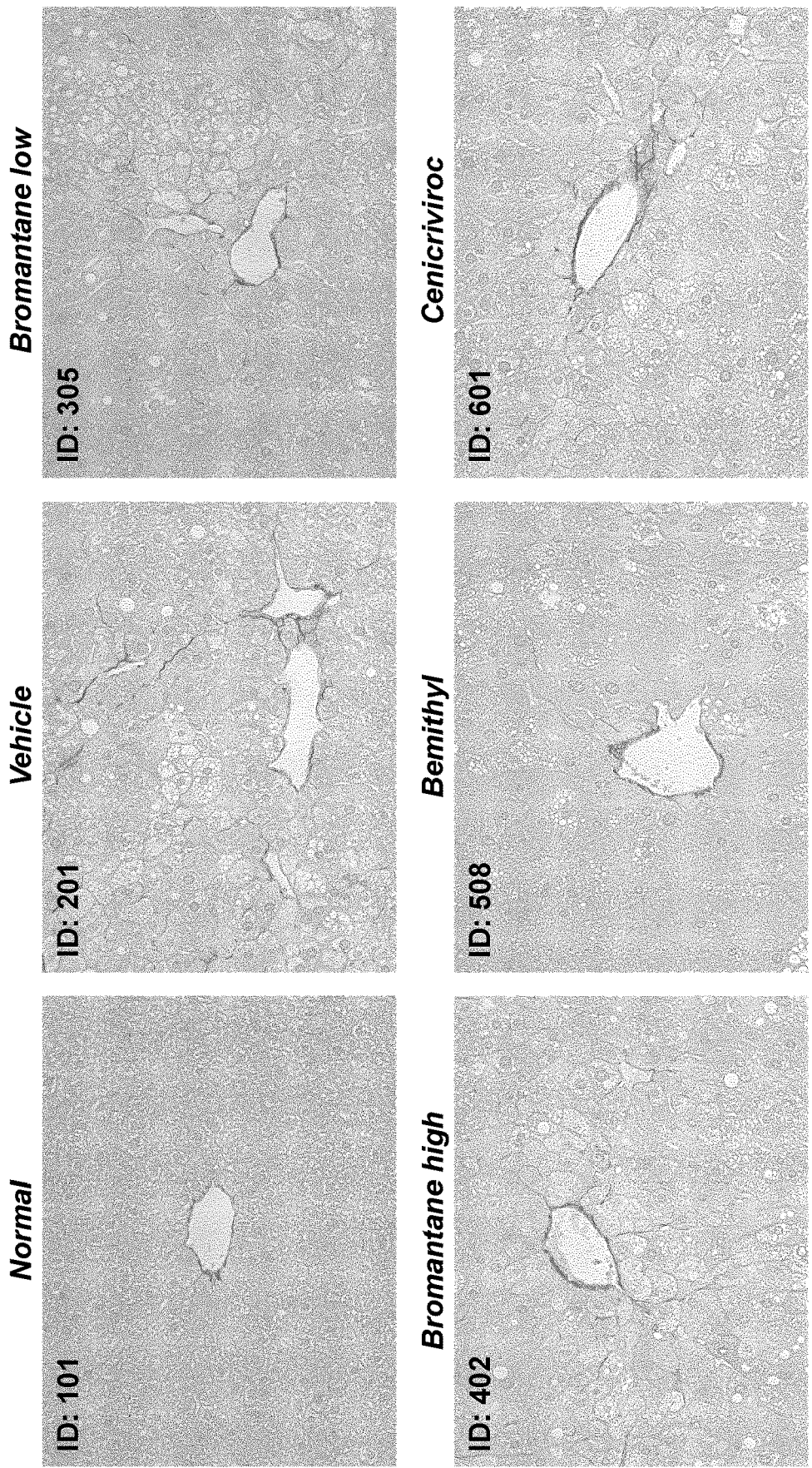
FIGS. 15a and 15b shows representative photomicrographs of Sirius red-stained liver sections for each of the 7 study groups of C57BL/6 mice consisting of the Normal (no NASH) group, the "Vehicle" control group and the 5 treatment groups including the positive control treatment group, Telmisartan. The panels are taken at ×200 magnification. The identity of each study group is listed above the upper panel in each pair of panels.
Figure 15B:
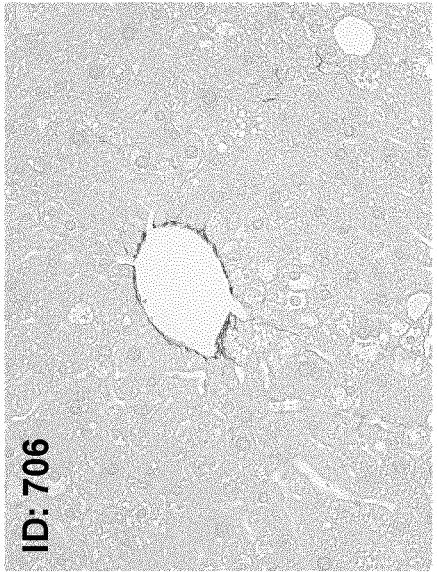
Figure 16:
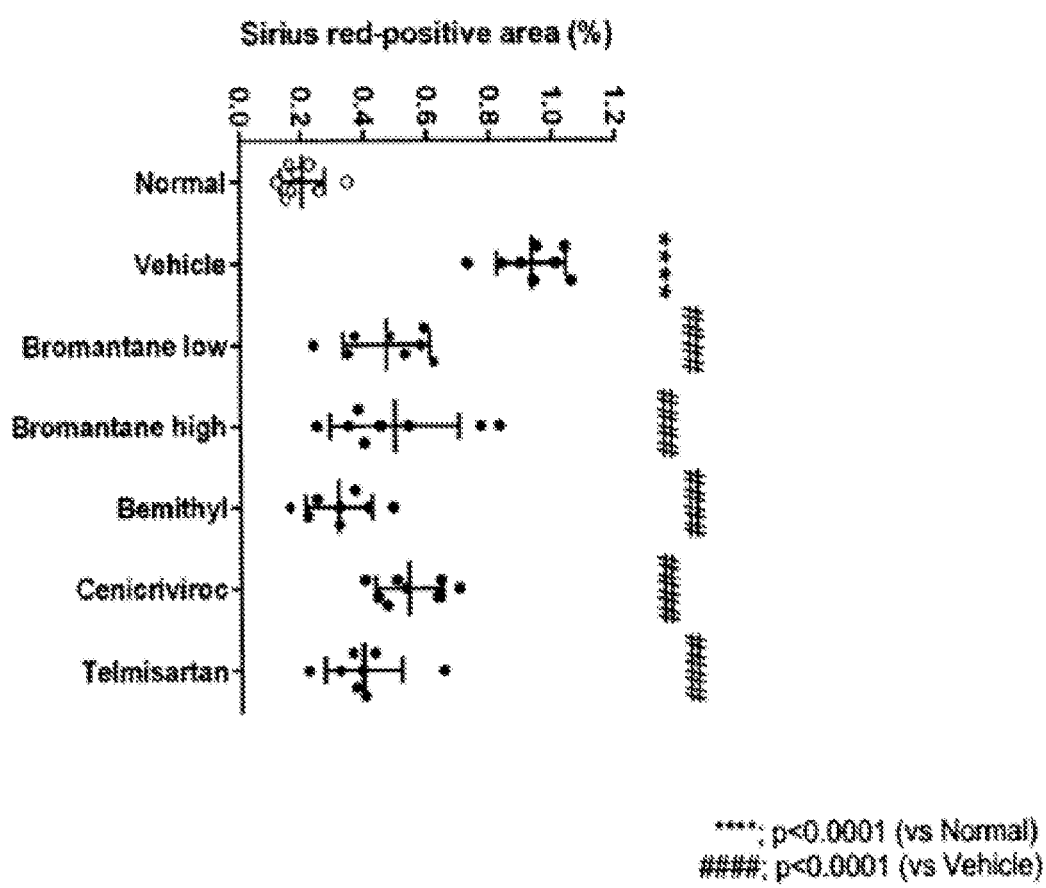
FIG. 16 shows an evaluation of liver function and disease progression consisting of the Fibrosis area, i.e. Sirius red-positive area in percentage of the 7 study groups of C57BL/6 mice consisting of the Normal (no NASH) group, the "Vehicle" control group and the 5 treatment groups including the positive control treatment group, Telmisartan. Mean is indicated±SD as determined using the Bonferroni multiple comparison test.

Steatohepatitis Evaluation: Steatohepatitis and disease progression was evaluated by H&E-staining of liver cross-sections as previously described. Representative photomicrographs of HE-stained liver sections for each of the 7 study groups are shown in FIGS. 10a-10c.

The NAFLD Activity Score of each study group consisted of the NAFLD Activity Score average of all mice in each study group. Scores were determined based on the steatosis score, lobular inflammation score and hepatocellular ballooning score for each animal. Results are summarized in FIGS. 11-14.

Statistically significant reductions in NAFLD activity score relative to Vehicle control were observed for the Bromantane high and Cenicriviroc treatment groups, as well as for the Telmisartan positive control. Statistically significant reductions in steatosis score relative to Vehicle control were observed for the Bromantane high treatment group, as well as for the Telmisartan positive control.

Significantly, all of the study groups, including the Bromantane low, Bromantane high, Bemithyl, and Cenicriviroc groups, showed statistically significant decreases in the fibrosis area (Sirius red-positive area) compared with the Vehicle group. The Bemithyl group showed particularly statistically significant decrease in fibrosis area. The fibrosis area in the Telmisartan group also tended to decrease compared with the Vehicle group.

The statistically significant and clinically relevant composite reduction in NAFLD Activity Scores, particularly for Bromantane high, Bemithyl and Cenicriviroc, suggest these compounds could be useful in preventing and/or treating NASH and its sequelae.

CONCLUSIONS

In conclusion, administration of the above test agents, especially Bromantane, Istradefylline, and Cenicriviroc, showed improvement in reducing the NAFLD Activity Scores, hepatic steatosis, lobular inflammation and hepatocellular ballooning and may be useful in the prophylaxis and/or treatment of NASH. In particular, the improvement was better with the groups treated with Bromantane at 40 mg/kg and Istradefylline at 18 mg/kg, followed by Cenicriviroc at 30 mg/kg.

Oral administration of Telmisartan at 10 mg/kg also showed improvement in the NAFLD Activity Scores, hepatic steatosis, lobular inflammation and hepatocellular ballooning as compared to the Vehicle group.

Throughout the description, specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

What is claimed is:

1. A method for the treatment or prophylaxis of non-alcoholic fatty liver disease in a subject, the method comprising administering a therapeutically effective amount of repirinast to the subject.

2. The method of claim 1, wherein the amount of repirinast is between 1 to 20 mg per kg of the subject.

3. The method of claim 2, wherein the amount of repirinast is between 3 to 10 mg per kg of the subject.

4. The method of claim 3, wherein the amount of repirinast is about 10 mg per kg of the subject.

5. The method of claim 1, wherein the non-alcoholic fatty liver disease is non-alcoholic steatohepatitis.

6. The method of claim 1, wherein the non-alcoholic fatty liver disease is non-alcoholic steatohepatitis-derived hepatocellular carcinoma.

* * * * *